United States Patent [19]

Bosies et al.

[11] 4,444,766
[45] Apr. 24, 1984

[54] SULFUR-CONTAINING PHOSPHOLIPID COMPOUNDS AND THERAPEUTIC COMPOSITIONS

[75] Inventors: Elmar Bosies, Weinheim; Rudi Gall, Hirschberg; Günter Weimann, Weinheim-Lützelsachsen; Uwe Bicker, Lorsch; Wulf Pahlke, Mannheim, all of Fed. Rep. of Germany

[73] Assignee: Boehringer Mannheim GmbH, Mannheim, Fed. Rep. of Germany

[21] Appl. No.: 311,830

[22] Filed: Oct. 16, 1981

[30] Foreign Application Priority Data

Oct. 21, 1980 [DE] Fed. Rep. of Germany ....... 3039629
May 13, 1981 [DE] Fed. Rep. of Germany ....... 3118965

[51] Int. Cl.³ ................. A61K 31/095; A61K 31/66; C07F 9/09
[52] U.S. Cl. ..................... 424/211; 260/941; 260/942; 260/945
[58] Field of Search ........ 260/945, 941, 922; 424/211

[56] References Cited

U.S. PATENT DOCUMENTS 3,694,473  9/1972  Eibl et al. ............................ 424/211
3,708,558  1/1973  Kny et al. ............................ 424/211
4,119,714 10/1978  Kny et al. ............................ 424/211
4,159,988  7/1979  Eibl et al. ............................ 260/945
4,329,302  5/1982  Hanahan et al. ..................... 260/945

FOREIGN PATENT DOCUMENTS 2642661  3/1978  Fed. Rep. of Germany ...... 260/945
1174399 12/1969  United Kingdom ................ 260/945

OTHER PUBLICATIONS

Derwent Abstract, Document No. 118-494, Japanese Patent to Toyama Chem. K.K. dated Sep. 11, 1980.
Schwartz et al., "Surface Active Agents", (1949), pp. 15–17, 41, 338, 189.

Primary Examiner—J. E. Evans
Attorney, Agent, or Firm—Felfe & Lynch

[57] ABSTRACT

Sulfur-containing phospholipid compounds of the formula

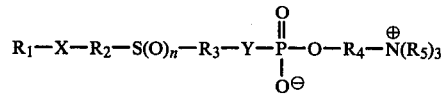

pharmaceutical compositions having anti-tumor activity which include said phospholipid compounds, and the method of use for combating tumors, of said phospholipid compounds.

21 Claims, No Drawings

SULFUR-CONTAINING PHOSPHOLIPID COMPOUNDS AND THERAPEUTIC COMPOSITIONS

This invention relates to new sulfur-containing phospholipids and the pharmacologically acceptable salts thereof, as well as pharmaceutical compositions containing them.

Federal Republic of Germany Pat. No. 2,009,341 describes 3-octadecyloxypropan-1-ol phosphoric acid monocholine ester as being an immunological adjuvant, Federal Republic of Germany Pat. No. 2,009,342 describes the 2-hydroxy derivative thereof as being an agent for increasing the natural resistance of the organism and Federal Republic of Germany Pat. No. 2,619,686 describes the 2-methoxy derivative as being an antitumour agent. Finally, Federal Republic of Germany Pat. No. 2,619,715 describes dodecyloxypropylphosphorylcholine as being a "tumour antigen".

We have now found that alkanolphosphoric acid monoammonium alkyl esters, which are substituted by an alkylated thio, sulphinyl or sulphonyl group have also a cancerostatic activity, but contrary to the conventional phospholipid materials, the compounds of the invention do not induce thrombocyte aggregation.

The present invention provides new compounds of the formula

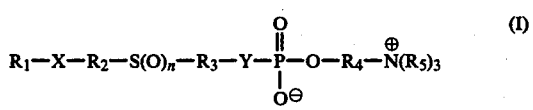

wherein X is a valency bond, an oxygen or sulphur atom, a sulphinyl or sulphonyl group, an aminocarbonyl, carbonylamino or ureido group or a cycloalkylene radical or a phenylene radical, Y is an oxygen or sulphur atom, $R_1$ is a hydrogen atom, a straight-chained or branched, saturated or unsaturated aliphatic hydrocarbon radical containing up to 18 carbon atoms, which is optionally substituted one or more times by aryl, halogen, lower alkoxy, alkylthio, alkoxycarbonyl, alkanesulphinyl or alkanesulphonyl, $R_2$ is a straight-chained or branched, saturated or unsaturated aliphatic hydrocarbon chain containing up to 18 carbon atoms, which is optionally substituted one or more times by halogen, aryl, lower alkoxy, alkoxycarbonyl, alkylthio, alkanesulphinyl or alkanesulphonyl, $R_3$ is a straight-chained or branched, saturated or unsaturated aliphatic hydrocarbon chain containing 2 to 8 carbon atoms, which can also be part of a cycloalkane ring and which is optionally substituted one or more times by hydroxy, halogen, nitrile, cycloalkyl, phenyl, alkoxycarbonyl, optionally alkylated carbamoyl, alkylthio, alkanesulphinyl, alkanesulphonyl, optionally acylated amino or by alkoxy which, in turn, can be substituted by aryl, alkylthio, alkanesulphinyl, alkanesulphonyl, optionally acylated amino, alkoxycarbonyl, nitrile, hydroxyl, alkoxy or optionally alkylated carbamoyl, $R_4$ is a straight-chained or branched alkylene chain containing 2 to 4 carbon atoms, $R_5$ is a hydrogen atom or a lower alkyl radical and n is 0, 1 or 2; as well as the pharmacologically acceptable salts thereof.

An alkyl substituent $R_5$ is a hydrocarbon radical containing up to 6 carbon atoms, especially a methyl or ethyl radical.

Alkoxy, alkoxycarbonyl, alkylthio, alkanesulphinyl and alkanesulphonyl mean, as a rule, radicals containing up to 6 carbon atoms but can also be radicals containing up to 20 carbon atoms, for example octadecylthio, tetradecyloxy, octylthio and the like.

When X is a cycloalkylene radical, it is to be understood to be a radical containing 3 to 8 carbon atoms and especially a cyclopropyl, cyclopentyl or cyclohexyl radical.

Cycloalkane rings, which can also be components of the alkylene chain of the group $R_3$, are preferably cyclopentane, cyclohexane and cycloheptane rings and the cycloalkane rings can also be further substituted by a lower alkyl radical.

Halogen means fluorine, chlorine, bromine and iodine, fluorine being preferred.

The group $R_1$—X—$R_2$—means, when X represents a valency bond, an alkylene chain with up to 20 carbon atoms, which can be straight-chained or branched and saturated or unsaturated. The straight-chained radical is preferably an eicosyl, octadecyl, heptadecyl, hexadecyl, tetradecyl, dodecyl or octyl radical. The unsaturated radical can contain up to 4 double bonds but preferably only contains 1 or 2 double bonds.

The group $R_3$ is preferably a —$CH_2$—$CH_2$—$CH_2$— radical, the middle —$CH_2$— group of which can be substituted once or twice by alkyl, alkoxy, alkylthio, alkanesulphinyl, alkanesulphonyl, alkoxyalkylene, benzyloxy, hydroxyl or halogen and which can optionally be substituted on the $C_1$ and $C_3$ by alkyl radicals, which can also be joined to form a ring.

The group $R_4$ is preferably a —$CH_2$—$CH_2$— radical.

Preferred compounds of general formula (I) are especially derivatives of propan-1-ol and propane-1-thiol phosphoric acid monocholine ester which are substituted in the 3-position of the propanol by an alkylthio, alkanesulphinyl or alkanesulphonyl radical and can possibly also be substituted in the 2-position.

The present invention also provides a process for the preparation of compounds of general formula (I), wherein a compound of the general formula:

$$R_1—X—R_2—S(O)_n—R_3—YH \qquad (II),$$

in which $R_1$, $R_2$, $R_3$, X, Y and n have the same meanings as above, is either (a) reacted with a compound of the general formula:

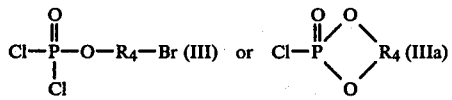

in which $R_4$ has the same meaning as above, in the presence of an acid-binding agent, selectively hydrolyzing the reaction product by use of a compound of Formula III and exchanging the remaining bromine atom for an optionally alkylated ammonium group, by use of a compound of Formula IIIa and direct reaction with optionally alkylated ammonia; or (b) converted into a compound of the general formula:

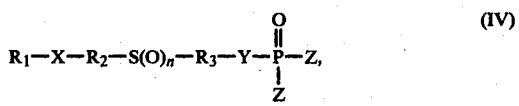

in which $R_1$, $R_2$, $R_3$, X, Y and n have the same meanings as above and Z is a hydroxyl group or a chlorine or bromine atom, and this then reacted with a compound of the general formula:

$$HO-R_4-N^{\oplus}(R_5)_3 \cdot Hal^{\ominus} \quad (V),$$

in which $R_4$ and $R_5$ have the same meanings as above and Hal $^{\ominus}$ is a chloride, bromide or iodide ion, in the presence of an acid-binding agent or of an activating reagent; or (c) reacted with a compound of the general formula:

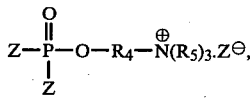

(VI)

in which $R_4$, $R_5$ and Z have the same meanings as above and Z $^{\ominus}$ is chloride or bromide ion, in the presence of an acid-binding agent, converted into an internal salt and optionally oxidised.

All the above-described processes are carried out in known manner.

Process (a) is usually carried out in such a manner that an alkanol or alkanethiol of general formula (II) is reacted with a bromoalkanol phosphoric acid monoester dichloride of general formula (III) in the presence of an acid-binding agent, for example triethylamine, in an anhydrous, inert organic solvent, for example a chlorinated hydrocarbon or toluene, at a temperature of from the freezing point to ambient temperature. The selective hydrolysis of the phosphoric acid diester monochloride obtained is achieved directly in the two-phase mixture by the addition of an aqueous potassium chloride solution at a temperature of from 0° to 50° C. For the substitution of the remaining bromine atom by an optionally alkylated ammonium group, ammonia or an alkylamine is dissolved in a medium which sufficiently readily dissolves not only the phosphoric acid diester but also ammonia or the amine, mixtures of acetonitrile or lower alcohols with chlorinated hydrocarbons being especially suitable, and the reaction is completed at a temperature of from 20° to 70° C.

In case of the use of a compound of Formula IIIa the reaction product is directly reacted with optionally alkylated ammonia.

It is also possible to proceed stepwise by first introducing an alkylammonium radical and subsequently reacting with an alkyl halide to give a di- or trialkylammonium alkyl ester.

The removal of the residual halide ions preferably takes place in a lower alcohol by means of silver acetate or silver oxide.

All the intermediates, as well as the end products, can be easily purified by column chromatography using conventional elution agents, for example, diethyl ether, ligroin, chlorinated hydrocarbons, lower alcohols or mixtures thereof, on silica gel. In the case of betaine-like end products, it is preferable to add some water to the elution agent used.

In the case of process (b), if Z signifies chlorine or bromine, the reaction of a compound of general formula (II) to give a phosphoric ester dihalide of general formula (IV) is carried out with a phosphorus oxyhalide in an inert, anhydrous solvent, for example, a halogenated hydrocarbon, in the presence of an acid acceptor, preferably of pyridine or quinoline. The reaction temperature is from 0° to 40° C. The product can be isolated or, without isolation, can be reacted with an alkylammonium alkanol halide or ammonium alkanol halide, with the addition of further pyridine or quinoline, at a temperature of from 0° to 40° C. to give the desired end product. The solvent for this reaction is preferably a halogenated hydrocarbon, acetonitrile or trichloroacetonitrile. If Z represents a hydroxyl group, a compound of general formula (IV) can be prepared by hydrolysis of the corresponding phosphoric ester dihalide or by hydrogenolysis of the corresponding phosphoric ester diphenyl ester. The further reaction with a compound of general formula (V) is carried out in the presence of a sulphonic acid halide, for example p-toluenesulphochloride or triisopropylbenzenesulphochloride. The solvent used can be dimethylformamide with an addition of pyridine or can also be pyridine alone. The reaction temperature is usually from 0° to 40° C.

The compounds of general formula (VI) in the case of process (c) can, when Z is a hydroxyl group, be reacted with generally used halogenation agents, for example phosphorus pentachloride, in the presence of an acid acceptor, for example pyridine, to give compounds of general formula (VI) in which Z is chlorine or bromine, which can then be isolated or, without isolation, can be reacted with compounds of general formula (II). The acid acceptors here employed are usually nitrogen-containing bases, for example pyridine, quinoline or triethylamine. The preferred solvents include anhydrous halogenated hydrocarbons, as well as toluene.

The alkylated mercaptoalkanols of general formula (II) used as starting materials are also new and can easily be obtained by reacting haloalkanes with mercaptocarboxylic acids or esters or by reacting mercaptoalkanes with halocarboxylic acids or esters in the presence of an acid-binding agent, for example a sodium alcoholate, in a lower alcohol or by adding mercaptoalkanes to $\alpha,\beta$-unsaturated carboxylic acids or esters in a lower alcohol with base catalysis and subsequently treating with a reducing agent, for example sodium borohydride, in a lower alcohol, or with lithium aluminium hydride in anhydrous diethyl ether. Further methods of preparing compounds of general formula (II) include reacting mercaptoalkanes with alkanols which contain a reactive group, for example a halogen atom or a sulphonic acid residue, or reacting haloalkanes with mercaptoalcohols in the presence of an acid-binding agent, for example potassium hydroxide or a sodium alcoholate, in a lower alcohol or by adding a mercaptoalkane to an unsaturated alcohol with base or peroxide catalysis.

The thiols of general formula (II) can be synthesised from alcohols of general formula (II) by known methods. Thus, for example, a halide or sulphonate can be prepared from an alcohol of general formula (II), this then reacted with thiourea and the resultant isothiuronium salt split with an alkali. Subsequent acidification then gives the desired thiol of general formula (II).

The present invention includes within its scope all stereoisomeric compounds of general formula (I) which, for example, are obtained on the basis of asymmetrical carbon atoms, the sulphoxide group or because of cis-trans isomerism. Products obtained as mixtures can be separated by means of known processes.

The pharmacologically acceptable salts are obtained in the usual manner, for example by neutralisation of compounds of general formula (I) with non-toxic inorganic or organic acids, for example hydrochloric acid, sulphuric acid, phosphoric acid, hydrobromic acid, acetic acid, lactic acid, citric acid, malic acid, salicylic acid, malonic acid, maleic acid or succinic acid.

The new compounds of general formula (I) according to the present invention can be administered enterally and parenterally in liquid or solid form. For this purpose, use can be made of all conventional forms of administration, for example tablets, capsules, dragees, syrups, solutions, suspensions and the like. As injection medium, it is preferred to use water which contains the additives usual in the case of injection solutions, such as stabilising agents, solubilising agents and/or buffers. Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Liquid carrier materials for injection solutions must be sterile and are preferably placed into ampoules. Solid carrier materials include, for example, starch, lactose, mannitol, methylcellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and/or sweetening agents.

The dosage used depends upon various factors, such as the mode of administration, species, age and/or individual condition. The dosage to be administered daily is usually from about 0.05 to 100 mg./kg. of body weight.

Preferred compounds according to the present invention are, apart from the compounds mentioned in the Examples and the compounds derivable therefrom by combination of all of the meanings given in the claims, also the following esters:

1. 2,3-Bis-(octadecylthio)-propan-1-ol phosphoric acid monocholine ester
2. 2-[3-(Hexadecylthio)-propoxyphosphoryloxyhydroxy]-2-methylethylammonium hydroxide
3. 3-Tetradecylthio-2-ethoxypropan-1-ol phosphoric acid monocholine ester
4. 3-Hexadecylthio-2-ethoxypropan-1-ol phosphoric acid monocholine ester; m.p. 69° C. sinters; 238°–243° C. decomp.
5. 3-(14-Methylthiotetradecylthio)-propan-1-ol phosphoric acid monocholine ester
6. 3-(17-Methyloctadecylthio)-propan-1-ol phosphoric acid monocholine ester
7. 3-(8-Fluorooctadecylthio)-propan-1-ol phosphoric acid monocholine ester
8. 2-Hydroxy-3-octadecylthiopropan-1-ol phosphoric acid monocholine ester
9. 2-Hydroxy-3-octadecanesulphinylpropan-1-ol phosphoric acid monocholine ester
10. 2-Hydroxy-3-octadecanesulphonylpropan-1-ol phosphoric acid monocholine ester
11. 2-Methoxy-3-[8-(4-octylcyclohexyl)-octylthio]-propan-1-ol phosphoric acid monocholine ester
12. 3-Hexadecylthio-2-methylthiopropan-1-ol phosphoric acid monocholine ester
13. 3-Hexadecylthio-2-methanesulphinylpropan-1-ol phosphoric acid monocholine ester
14. 3-Hexadecylthio-2-methanesulphonyl-propan-1-ol phosphoric acid monocholine ester
15. 2-Methoxy-3-(2-methoxyoctadecylthio)-propan-1-ol phosphoric acid monocholine ester
16. 2-Methoxy-3-(2-tetradecyloxyoctadecylthio)-propan-1-ol phosphoric acid monocholine ester
17. 2-Methoxy-3-(14-methoxytetradecylthio)-propan-1-ol phosphoric acid monocholine ester
18. 2-Methoxy-3-(14-methylthiotetradecylthio)-propan-1-ol phosphoric acid monocholine ester
19. 2-Methoxy-3-(17-methyloctadecylthio)-propan-1-ol phosphoric acid monocholine ester
20. 3-(8-Fluorooctadecylthio)-2-methoxypropan-1-ol phosphoric acid monocholine ester
21. 2-Fluoro-3-octadecylthiopropan-1-ol phosphoric acid monocholine ester
22. 2-Fluoro-3-octadecanesulphinylpropan-1-ol phosphoric acid monocholine ester
23. 2-Fluoro-3-octadecanesulphonylpropan-1-ol phosphoric acid monocholine ester
24. 2-Ethylthio-3-octadecylthiopropan-1-ol phosphoric acid monocholine ester
25. 3-Hexadecanesulphinyl-2-methylpropan-1-ol phosphoric acid monocholine ester
26. 3-Heptadecylthio-2-methylpropan-1-ol phosphoric acid monocholine ester; m.p. 74° C. sinters; 250°–254° C. decomp.
27. Cis-3-Hexadecylthio-cyclohexanol-1-ol phosphoric acid monocholine ester; m.p. 65° C. sinters; 240°–252° C. decomp.
28. 2,3-Bis-(octylthio)-propan-1-ol phosphoric acid monocholine ester
29. 2-Methoxy-3-[8-(4-octylphenyl)-octylthio]-propan-1-ol phosphoric acid monocholine ester
30. 2,2-Dimethyl-3-hexadecanesulphinylpropan-1-ol phosphoric acid monocholine ester
31. 2,2-Dimethyl-3-hexadecanesulphonylpropan-1-ol phosphoric acid monocholine ester
32. 2-Methoxymethylene-3-octadecylthiopropan-1-ol phosphoric acid monocholine ester
33. 2,2-Diethoxy-3-hexadecylthiopropan-1-ol phosphoric acid monocholine ester
34. 4-Octadecylthio-n-butan-2-ol phosphoric acid monocholine ester
35. 4-Octadecanesulphinyl-n-butan-1-ol phosphoric acid monocholine ester
36. 4-Octadecanesulphonyl-n-butan-1-ol phosphoric acid monocholine ester
37. 3-Hexadecanesulphinylcyclopentan-1-ol phosphoric acid monocholine ester
38. 3-Hexadecanesulphonylcyclopentan-1-ol phosphoric acid monocholine ester
39. 4-Octadecylthio-n-butan-1-ol phosphoric acid monocholine ester
40. 3-Octadecanesulphinylcyclohexan-1-ol phosphoric acid monocholine ester
41. 3-Octadecanesulphonylcyclohexan-1-ol phosphoric acid monocholine ester
42. 2-Ethyl-3-octadecylthiocyclohexan-1-ol phosphoric acid monocholine ester
43. 2,2-(6-Methylcyclohex-3-enylidene)-3-hexadecylthio-propan-1-ol phosphoric acid monocholine ester
44. 2-Octadecylthioethanol phosphoric acid monocholine ester
45. 2-(2-Propynyl)-3-hexadecylthiopropan-1-ol phosphoric acid monocholine ester; m.p. 54° C. sinters; 237°–239° C. decomp.

46. 2-(1-Propynyl)-3-hexadecylthiopropan-1-ol phosphoric acid monocholine ester
47. 2-Propadienyl-3-hexadecylthiopropan-1-ol phosphoric acid monocholine ester
48. 2-(1-Propenyl)-3-hexadecylthiopropan-1-ol phosphoric acid monocholine ester
49. 2-(1-Methyl-2-propynyl)-3-hexadecylthiopropan-1-ol phosphoric acid monocholine ester
50. Trans-3-hexadecylthiocyclohexan-1-ol phosphoric acid monocholine ester; m.p. 59° C. sinters; 245°–250° C. decomp.
51. 2-Isopropyl-3-hexadecylthiopropan-1-ol phosphoric acid monocholine ester; m.p. 68° C. sinters; 242° C. decomp.
52. 2-Methyl-3-heptadecylthiopropan-1-ol phosphoric acid monocholine ester
53. 2-Methyl-3-hexadecanesulphonylpropan-1-ol phosphoric acid monocholine ester; m.p. 64° C. sinters; 232° C. foams
54. 2-Methyl-2-methoxy-3-hexadecylthiopropan-1-ol phosphoric acid monocholine ester
55. 2,2-Bis-(methoxymethyl)-hexadecylthiopropan-1-ol phosphoric acid monocholine ester
56. 2-Cyclopropyl-3-hexadecylthiopropan-1-ol phosphoric acid monocholine ester
57. 2-Methylthiomethyl-3-hexadecylthiopropan-1-ol phosphoric acid monocholine ester; wax; decomp. point 240° C.
58. 2-Methanesulphinylmethyl-3-hexadecylthiopropan-1-ol phosphoric acid monocholine ester
59. 2-Methanesulphonylmethyl-3-hexadecylthiopropan-1-ol phosphoric acid monocholine ester
60. 2-Methoxyethoxymethyl-3-hexadecylthiopropan-1-ol phosphoric acid monocholine ester
61. 2-Cyanomethyl-3-hexadecylthiopropan-1-ol phosphoric acid monocholine ester
62. 2-Carbamoylmethyl-3-hexadecylthiopropan-1-ol phosphoric acid monocholine ester
63. 2-(N,N-Dimethylcarbamoylmethyl)-3-hexadecylthiopropan-1-ol phosphoric acid monocholine ester
64. 2-Ethoxycarbonylmethyl-3-hexadecylthiopropan-1-ol phosphoric acid monocholine ester
65. 2-Methyl-3-(1-methoxycarbonylheptadecylthio)-propan-1-ol phosphoric acid monocholine ester; m.p. 84° C. sinters, 239°–241° C. foams
66. 2-(2,2,2-Trifluoroethoxy)-3-hexadecylthiopropan-1-ol phosphoric acid monocholine ester
67. Thiophosphoric acid O-choline ester S-3-heptadecylthiopropyl ester; m.p. 80° C. sinters; 264° C. decomp.
68. Thiophosphoric acid O-choline ester S-2-methyl-3-hexadecanesulphinylpropyl ester
69. Thiophosphoric acid O-choline ester S-2-methyl-3-hexadecanesulphonylpropyl ester ; m.p. 60° C. sinters; 205°–208° C. foams
70. Thiophosphoric acid O-choline ester S-2-benzyl-3-octadecylthiopropyl ester ; m.p. 240° C. decomp.
71. Thiophosphoric acid O-choline ester S-2,2-dimethyl-3-hexadecylthiopropyl ester
72. 2-Aminoethyl-3-hexadecylthiopropan-1-ol phosphoric acid monocholine ester
73. 2-Acetylaminoethyl-3-hexadecylthiopropan-1-ol phosphoric acid monocholine ester
74. 2-Mesylaminoethyl-3-hexadecylthiopropan-1-ol phosphoric acid monocholine ester
75. 2-Hydroxymethyl-3-heptadecylthiopropan-1-ol phosphoric acid monocholine ester
76. 2-Cyclopentyl-3-heptadecylthiopropan-1-ol phosphoric acid monocholine ester
77. 2-Cyclohexylmethyl-3-hexadecylthiopropan-1-ol phosphoric acid monocholine ester
78. 2-p-Methylbenzyl-3-octadecylthiopropan-1-ol phosphoric acid monocholine ester
79. 2-(2-Methoxy-5-chlorobenzyl)-3-octadecylthiopropan-1-ol phosphoric acid monocholine ester
80. 2-Cyano-3-heptadecylthiopropan-1-ol phosphoric acid monocholine ester
81. 2-Carbamoyl-3-heptadecylthiopropan-1-ol phosphoric acid monocholine ester
82. 2-Hydroxy-3-hexadecylthiopropan-1-ol phosphoric acid monocholine ester
83. 2-Isopropoxy-3-heptadecylthiopropan-1-ol phosphoric acid monocholine ester
84. 2-(2-Phenethyloxy)-3-heptadecylthiopropan-1-ol phosphoric acid monocholine ester
85. 2-(2-Hydroxyethoxy)-3-octadecylthiopropan-1-ol phosphoric acid monocholine ester
86. 2-(2-Methylthioethoxy)-3-octadecylthiopropan-1-ol phosphoric acid monocholine ester
87. 2-(2-Methanesulphinylethoxy)-3-octadeculthiopropan-1-ol phosphoric acid monocholine ester
88. 2-(2-Methanesulphonylethoxy)-3-octadecylthiopropan-1-ol phosphoric acid monocholine ester
89. 2-(2-Aminoethoxy)-3-heptadecylthiopropan-1-ol phosphoric acid monocholine ester
90. 2-(2-Acetylaminoethoxy)-3-heptadecylthiopropan-1-ol phosphoric acid monocholine ester
91. 2-(2-Mesylaminoethoxy)-3-heptadecylthiopropan-1-ol phosphoric acid monocholine ester
92. 2-Ethoxycarbonylmethoxy-3-hexadecylthiopropan-1-ol phosphoric acid monocholine ester
93. 2-Cyanomethoxy-3-hexadecylthiopropan-1-ol phosphoric acid monocholine ester
94. 2-Carbamoylmethoxy-3-hexadecylthiopropan-1-ol phosphoric acid monocholine ester
95. 2-Amino-3-hexadecylthiopropan-1-ol phosphoric acid monocholine ester
96. 2-Acetylamino-3-hexadecylthiopropan-1-ol phosphoric acid monocholine ester
97. 2-Methyl-3-(11-butylureyleneundecylthio)-propan-1-ol phosphoric acid monocholine ester
98. 2-Methyl-3-(11-valeroylaminoundecylthio)-propan-1-ol phosphoric acid monocholine ester
99. 2-N-Dodecylcarboxamidomethoxy-3-hexadecylthio-propan-1-ol phosphoric acid monocholine ester
100. 2-Ethylidene-3-hexadecylthiopropan-1-ol phosphoric acid monocholine ester
101. Cyclopropane-1-hexadecylthiomethyl-1-methanol phosphoric acid monocholine ester.

The following Examples, which are given for the purpose of illustrating the present invention, illustrate some of the process variants which can be used for preparing the compounds according to the present invention:

EXAMPLE 1

3-Octadecylthiopropan-1-ol phosphoric acid monocholine ester 6.7 g. 3-Octadecylthiopropanol (m.p. 53°–55° C.) are dissolved in 70 ml. anhydrous methylene chloride and added dropwise at −5° C. to a second solution which contains 6.7 g. phosphoric acid mono-2-bromoethyl ester dichloride and 9.7 ml. triethylamine in 70 ml. anhydrous methylene chloride. After 1 hour, the temperature is allowed to rise to ambient temperature and the reaction mixture left to stand overnight. 80 ml. 0.1N Potassium chloride solution are then added thereto and the reaction mixture stirred for 2 hours at 40° C. It is then cooled, 130 ml. methanol are added thereto and the pH is adjusted to 3 with concentrated hydrochloric acid. The organic phase is separated off, washed with water, dried and evaporated. The evaporation residue (8.7 g.), which is 3-octadecylthiopropan-1-ol phosphoric acid mono-(2-bromoethyl) ester, is further reacted in a crude state. It is dissolved in a mixture of 45 ml. each of methanol and chloroform and trimethylamine passed therein. The reaction mixture is then stirred under reflux for 1 hour, left to stand overnight at ambient temperature, evaporated, the residue dissolved in chloroform, filtered and the clear filtrate mixed with acetone, 6.1 g. thin layer chromatographically uniform bromide thereby being obtained. For the removal of the bromide ion, the bromide is treated in methanolic solution with silver acetate and thereafter purified on a silica gel column by elution with a mixture of chloroform-methanol-water (65:25:4 v/v/v). The desired compound is thus obtained in a yield of 2.3 g. (26% of theory); m.p. 238°–240° C. (decomp.).

According to the results of elementary analysis, the product contains 1.5 mole of water.

The structure is verified by the NMR spectrum and by elementary analysis and that of the preliminary stages also by mass spectroscopic investigation here and in all of the other Examples.

The 3-octadecylthiopropanol used as starting material is prepared in the following manner:

0.35 g. of sodium are dissolved in 10 ml. methanol, 1.8 g. methyl 3-mercaptopropionate are added dropwise thereto, and then a solution of 5.2 g. octadecyl bromide in 20 ml. methanol is added. After boiling under reflux for 3 hours, the reaction mixture is cooled and the suspension obtained is filtered off with suction. It is purified by chromatographing on a silica gel column, using as elution agent chloroform-ligroin (1:1 v/v). There are obtained 4.1 g. methyl 3-octadecylthiopropionate; m.p. 39°–41° C. This is dissolved in diethyl ether and reduced with lithium aluminium hydride until the ester can no longer be detected in the thin later chromatogram. After working up in the usual way, there are thus obtained 2.8 g. 3-octadecylthiopropanol; m.p. 53°–55° C.

Instead of octadecyl bromide, there can also be used octadecyl mercaptan which is then reacted with methyl 3-bromopropionate or added on to methyl acrylate with sodium methylate catalysis. In both cases, methyl 3-octadecylthiopropionate is obtained.

Finally, 3-octadecylthiopropanol can also be obtained by the addition of octadecyl mercaptan to allyl alcohol.

EXAMPLE 2

3-Octadecanesulphinylpropan-1-ol phosphoric acid monocholine ester 0.25 g. of the preliminary stage described in Example 1, i.e. 3-octadecylthiopropanol, is mixed in 5 ml. glacial acetic acid with 0.07 ml. perhydrol. After stirring for 1 hour at ambient temperature, the reaction mixture is rendered weakly alkaline with a dilute aqueous solution of sodium hydroxide and the suspension, after 2 hours, then filtered off with suction, washed with water and dried. There is thus obtained 0.34 g. 3-(octadecanesulphinyl)-propanol (m.p. 74°–78° C.) which is purified on a silica gel column with chloroform-methanol (99:1 v/v), which brings about an increase of the m.p. to 81°–83° C. The synthesis is continued with this compound in the manner described in Example 1. There is thus obtained a yield of 19% of theory of thin layer chromatographically uniform crystals of the desired compound; m.p. 244° C. (decomp.). It contains 1 mole of water.

An identical product is also obtained by the selective oxidation of the compound obtained in Example 1, using perhydrol in glacial acetic acid.

EXAMPLE 3

3-Octadecanesulphonylpropan-1-ol phosphoric acid monocholine ester 0.25 g. of the compound described in Example 1 is stirred in 5 ml. glacial acetic acid and 0.1 ml. of perhydrol for 8 hours at ambient temperature. After the addition of water, the reaction mixture is then evaporated and the residue stirred up with acetone. There is thus obtained 0.23 g. (87% of theory) of the desired compound in the form of crystals; m.p. 240°–242° C. They contain 2 mole of water.

The identical product is also obtained in the following manner:

0.5 g. of the preliminary stage described in Example 1, i.e 3-octadecylthiopropanol, is dissolved in 10 ml. glacial acetic acid and mixed with 0.13 ml. perhydrol. After stirring for 1 hour at ambient temperature, the addition of hydrogen peroxide is repeated and the reaction mixture is left to stand for 24 hours. The resultant suspension is then filtered off with suction and the 0.3 g. of crystals obtained purified on a column; m.p. 92°–94° C.

With this compound, the synthesis is carried out in a manner analogous to that described in Example 1. In the thin layer chromatogram, the sulphone can be differentiated not only from the sulphoxide but also from the mercapto compound by means of the $R_F$ value. In the case of monitoring of the course of the reaction, it can be shown that, as intermediate stage, there is formed, in the case of both methods, the sulphoxide described in Example 2.

EXAMPLE 4

3-(Octadec-9t-enylthio)-propan-1-ol phosphoric acid monocholine ester

Methyl 3-(octadec-9t-enylthio)-propionate is obtained in a yield of 69% of theory in the form of an oil, using the method of working described in Example 1 and employing elaidine bromide. Lithium aluminium hydride reduction gives a yield of 83% of theory of 3-(octadec-9t-enylthio)-propanol (m.p. 38°–40° C.) which is phosphorylated and reacted with trimethylamine in the manner described in Example 1. The yield is 9%; m.p. 238°–243° C. The product contains 2 mole of water.

EXAMPLE 5

3-(Octadec-9t-enesulphonyl)-propan-1-ol phosphoric acid monocholine ester 1.4 g. of the compound obtained in Example 4 is dissolved in 35 ml. glacial acetic acid, 0.5 ml. perhydrol is added thereto in 2 portions in the course of 2 hours and the reaction mixture is left to stand for 24 hours at ambient temperature. It is then mixed with water, evaporated and the residue is taken up in chloroform and precipitated out with diethyl ether. A melting point cannot be determined on the amorphous, hygroscopic product obtained. According to the analysis, it contains 3 mole of water.

EXAMPLE 6

3-Hexadecylthiopropan-1-ol phosphoric acid monocholine ester

According to the procedure described in Example 1, with 1-hexadecyl bromide there is obtained methyl β-hexadecylthiopropionate in a yield of 88% of theory (hygroscopic crystals) and from this, by reduction with lithium aluminium hydride, there is obtained a yield of 95% of theory of 3-hexadecylthiopropanol; m.p. 50°–51° C. Subsequent phosphorylation and reaction with trimethylamine gives the desired product in a yield of 11% of theory. The thin layer chromatographically uniform crystals have a melting point of 240° C. (decomp.). They contain 2.5 mole of water.

EXAMPLE 7

3-Hexadecanesulphonylpropan-1-ol phosphoric acid monocholine ester

Oxidation of the compound described in the preceding Example with 30% hydrogen peroxide in glacial acetic acid gives the desired compound in a yield of 70% of theory. A melting point determination cannot be carried out because the product becomes sticky in the air. It contains 1.5 mole of water.

EXAMPLE 8

3-(3,7,11,15-Tetramethylhexadecylthio)-propan-1-ol phosphoric acid monocholine ester 1-Bromo-3,7,11,15-tetramethylhexadecane (prepared as described in Helv. Chim. Acta, 12, 915/1929) is reacted with ethyl β-mercaptopropionate in a manner analogous to that described in Example 1. The reaction product is obtained in the form of a yellowish oil in a yield of 82% of theory. It is then reduced with lithium aluminium hydride, the reduction product being obtained in the form of a yellowish oil in a yield of 90% of theory. It is subsequently phosphorylated and reacted with trimethylamine. After purification in the usual manner, the desired end product is obtained in the form of an amorphous substance in a yield of 15% of theory. The product contains 3 moles of water.

EXAMPLE 9

3-(3,7,11,15-Tetramethylhexadecanesulphonyl)-propan-1-ol phosphoric acid monocholine ester The product of Example 8 is oxidised in the manner described in Example 3 to give the desired product in a yield of 86% of theory It is also obtained in an amorphous state and contains 2 moles of water.

EXAMPLE 10

3-Heptadecylthiopropan-1-ol phosphoric acid monocholine ester

The following reactions are carried out in a manner analogous to that described in Example 1.

1-Bromoheptadecane is reacted with methyl β-mercaptopropionate to give the intermediate ester in the form of an oil in a yield of 88% of theory. This ester is reduced with lithium aluminium hydride to give 3-heptadecylthiopropanol in a yield of 88% of theory (m.p. 48°–51° C.). Subsequent phosphorylation and reaction with trimethylamine gives the desired end product in a yield of 21% of theory; m.p. 246° C. (decomp.). It contains 1 mole of water.

EXAMPLE 11

3-Heptadecanesulphonylpropan-1-ol phosphoric acid monocholine ester

The product of Example 10 is oxidised in the usual manner with hydrogen peroxide in glacial acetic acid to give the desired product in a yield of 76% of theory. A melting point determination is not possible because the product is sticky. It contains 2 moles of water.

EXAMPLE 12

3-Eicosylthiopropan-1-ol phosphoric acid monocholine ester

The reaction of eicosyl bromide with methyl β-mercaptopropionate is carried out in a manner analogous to that described in Example 1. The intermediate is obtained in a yield of 74% of theory; m.p. 48°–50° C. In the subsequent reaction steps, which are also carried out in a manner analogous to that described in Example 1, the reduction with lithium aluminium hydride gives a yield of 76% of theory of 3-eicosylthiopropanol (m.p. 58°–60° C. ) which, after subsequent phosphorylation and choline formation, gives the desired end product in a yield of 16% of theory; m.p. 235°–238° C. (decomp.). It contains 2 moles of water.

EXAMPLE 13

3-Eicosanesulphonylpropan-1-ol phosphoric acid monocholine ester

The product of Example 12 is oxidised at ambient temperature with perhydrol in glacial acetic acid. The crystalline product is obtained in a yield of 76% of theory; m.p. 210°–229° C. (decomp.). The crystals contain 3 moles of water.

EXAMPLE 14

3-Dodecylthiopropan-1-ol phosphoric acid monocholine ester

The synthesis is also carried out in a manner analogous to that of Example 1. Methyl β-dodecylthiopropionate is obtained in the form of an oil in quantitative yield and from this is obtained 3-dodecylthiopropanol in a yield of 94%, this substance being initially obtained in the form of an oil which solidifies upon cooling. Subsequent phosphorylation and choline formation gives the desired end product in a yield of 16% of theory: m.p. 229°–231° C. (decomp.). The product contains 1 mole of water.

EXAMPLE 15

3-Dodecanesulphonylpropan-1-ol phosphoric acid monocholine ester

The product of Example 14 is oxidised in the usual way with hydrogen peroxide in glacial acetic acid. The desired product is obtained in a yield of 74% of theory; m.p. 95°–99° C. (decomp.). The product contains 2 moles of water.

EXAMPLE 16

3-(2-Pentadecyloxyethylthio)-propan-1-ol phosphoric acid monocholine ester 2.8 g. Sodium are dissolved in 34 ml. ethylene glycol, 53.5 ml. 1-bromopentadecane are added thereto and the reaction mixture is stirred for 15 hours at 150° C. After cooling, it is extracted with ethyl acetate-ligroin (1:2 v/v), the extracts are evaporated and the residue is chromatographed on a silica gel column with ligroin. The desired intermediate is obtained as an oil which solidifies upon standing. The yield is 29% of theory.

10 g. of this intermediate are stirred for 5 hours at ambient temperature with 1.4 ml. phosphorus tribromide and 0.6 ml. pyridine, then poured on to ice, extracted with diethyl ether and purified on a column to give a yield of 60% of theory of 1-(2-bromoethoxy)-pentadecane in the form of an oil.

Subsequent reaction in a manner analogous to that described in Example 1 gives methyl β-(2-pentadecyloxyethylthio)-propionate in a yield of 69% of theory, from which is obtained 3-(2-pentadecyloxyethylthio)-propanol in a yield of 95% of theory; m.p. 44°–47° C. After reaction with bromoethyl phosphoric acid dichloride and then with trimethylamine, the desired product is obtained in a yield of 31% of theory; m.p. 231°–233° C. (decomp.). It contains 1 mole of water.

EXAMPLE 17

3-(2-Pentadecyloxy)-ethanesulphonylpropan-1-ol phosphoric acid monocholine ester The product of Example 16 is oxidised in the usual way with perhydrol in glacial acetic acid. The reaction mixture is mixed with water, evaporated and the residue stirred with diethyl ether in order to bring about crystallisation. The desired product is obtained as hygroscopic crystals in a yield of 75% of theory. The product has a decomposition point of 95° C. It contains 2 moles of water.

EXAMPLE 18

3-[3-(Octadecanesulphonyl)-propoxyphosphoryloxyhydroxy]-propyltrimethylammonium hydroxide 3-Bromopropan-1-ol is reacted with phosphorus oxychloride in a manner analogous to that described in Helv. Chim. Acta, 33, 349/1958 for 2-bromoethanol and the ester dichloride obtained (b.p. 130°–134° C./17 mm.Hg) reacted in the manner described in Example 1 with the 3-(octadecanesulphonyl)-propanol described in Example 3. After subsequent reaction with trimethylamine, the desired product is obtained in a yield of 25% of theory; m.p. 226°–229° C. (decomp.).

EXAMPLE 19

2-[3-(Octadecanesulphonyl)-propoxyphosphorylhydroxy]-2-methylethyltrimethylammonium hydroxide 1-Bromopropan-2-ol is reacted with phosphorus oxychloride in a manner analogous to that described in Helv. Chim. Acta, 33, 349/1958 for 2-bromoethanol and the ester dichloride obtained (b.p. 110° C./18 mm.Hg) reacted in the manner described in Example 1 with the 3-(octadecanesulphonyl)-propanol described in Example 3. After subsequent reaction with trimethylamine, the desired product is obtained in a yield of 3.1% of theory; m.p. 203° C. (decomp.). It crystallises with 2 moles of water.

EXAMPLE 20

2-Methoxy-3-octadecylthiopropan-1-ol phosphoric acid monocholine ester

A. 7.7 ml. Benzenesulphochloride are added dropwise at 0° C., while stirring, to 6.37 g. 2-0-methylglycerol in 70 ml. anhydrous pyridine. The reaction mixture is left to stand overnight in a refrigerator and then poured on to 150 g. of ice. The aqueous phase is extracted with methylene chloride, the organic phase is shaken up with 2 N hydrochloric acid, aqueous sodium bicarbonate solution and water and then dried and evaporated. The residue is applied to a silica gel column (500 g.; elution agent toluene-acetone 3:1 v/v). There are obtained 7.2 g. (about 48.6% of theory) 2-0-methylglycerol monobenzenesulphonate in the form of an oil.

B. 1.74 g. Solid potassium hydroxide is dissolved in 60 ml. absolute ethanol. A solution of 8.88 g. octadecylmercaptan in 60 ml. absolute ethanol is added dropwise at ambient temperature, while stirring. After 1 hour, a solution of 6.93 g. 2-0-methylglycerol monobenzenesulphonate in 30 ml. absolute ethanol is added dropwise thereto, followed by stirring for 1.5 hours at ambient temperature. The reaction mixture is subsequently poured into 1 liter of ice water, acidified with 2 N hydrochloric acid, extracted with diethyl ether and the organic phase is dried and evaporated. The residue is purified over a silica gel column (500 g.; elution agent diethyl ether-ligroin 1:1 v/v). There are obtained 6.1 g. (about 58% of theory) 2-methoxy-3-octadecylthiopropanol; m.p. 44°–47° C.

C. 5.67 g. Triethylamine are added to 6.0 g. 2-methoxy-3-octadecylthiopropanol in 80 ml. anhydrous toluene and a solution of 4.91 g. 2-bromoethylphosphoric acid dichloride in 50 ml. anhydrous toluene added dropwise thereto, while stirring, at 0° C. After 4 hours at 0° C., the reaction mixture is stirred overnight at ambient temperature, cooled to 0° C., 67 ml. 0.1 N aqueous potassium chloride solution are added thereto and the reaction mixture then vigorously stirred for 1 hour at 0° C. and for 2 hours at ambient temperature. The toluene phase is separated off, dried and evaporated. The residue is taken up in 45 ml. anhydrous methanol/30 ml. anhydrous chloroform, filtered and the solution saturated with dry trimethylamine. It is then boiled under reflux for 16 hours and subsequently evaporated. The residue is taken up in 180 ml. anhydrous methanol, mixed with 2.88 g. silver acetate, stirred for 1.5 hours at ambient temperature, filtered with suction, then washed with anhydrous methanol and the filtrate evaporated. The residue is purified over a silica gel column (100 g.; elution agent chloroform-methanol-water 65:25:4 v/v/v). There is thus obtained 1.8 g. (about 19.6% of theory) of the desired 2-methoxy-3-octadecylthiopropan-1-ol phosphoric acid monocholine ester. The amorphous product obtained is crystallised by dissolving in anhydrous chloroform and precipitating out with acetone; m.p 251°–252° C. The product contains 2 moles of water.

EXAMPLE 21

2-Methoxy-3-octadecanesulphinylpropan-1-ol phosphoric acid monocholine ester.

2-Methoxy-3-octadecylthiopropan-1-ol phosphoric acid monocholine ester is treated with 30% hydrogen peroxide in glacial acetic acid in the manner described in Example 2. The crude product obtained is triturated several times with acetone and thus brought to crystallisation. It sinters at 81° C., liquifies at 120°–122° C. and decomposes at 270°–272° C. The yield is 75.7% of theory. The product contains 2 moles of water.

EXAMPLE 22

2-Methoxy-3-octadecanesulphonylpropan-1-ol phosphoric acid monocholine ester

2-Methoxy-3-octadecylthiopropan-1-ol phosphoric acid monocholine ester is treated with 30% hydrogen peroxide in glacial acetic acid in the manner described in Example 3. The crude product is triturated several times with acetone and thus brought to crystallisation The yield is 73.5% of theory. A melting point cannot be determined. The product contains 2 moles of water.

EXAMPLE 23

3-(2-Pentadecylthioethylthio)-propan-1-ol phosphoric acid monocholine ester

Starting from 3-(2-pentadecylthioethylthio)-propanol (m.p. 53°–55° C.) and using the procedure described in Example 1, the desired product is obtained in the form of hygroscopic crystals which contain 2 mole of water and have a decomposition point of 237° C.

The starting material is obtained in the following manner:

A solution of 2.3 g. sodium in 80 ml. methanol, which contains 12 g. methyl 3-mercaptopropionate and 12.5 g. 2-bromoethanol, is stirred under reflux for 4 hours. After evaporating, the residue is taken up in chloroform, filtered and evaporated. 16 g. Methyl 3-(2-hydroxyethylthio)-propionate are obtained in the form of an oil.

8.2 g. of this ester are dissolved in 27 ml. anhydrous diethyl ether, 0.8 ml. pyridine is added thereto and then 1.9 ml. phosphorus tribromide is added dropwise, while cooling with ice. The reaction mixture is subsequently stirred for 5 hours at ambient temperature. Ice water is then added thereto, followed by extraction with diethyl ether. The extract is washed with water, dried and evaporated to give 10.1 g. of an oil which is chromatographed with 480 g. of silica gel, using ligroin-diethyl ether (2:1 v/v) as elution agent, 7.1 g. methyl 3-(2-bromoethylthio)-propionate being obtained in the form of an oil.

A solution of 0.6 g. sodium in 30 ml. methanol, which contains 6.3 g. 1-mercaptopentadecane and 5.9 g. of the above ester, is heated under reflux for 3 hours. The reaction mixture is then cooled and, after dissolving in diethyl ether, filtering and evaporating, there are obtained 9.4 g. of crystalline methyl 3-(2-pentadecylthioethylthio)-propionate, which are dissolved in 80 ml. anhydrous diethyl ether and added dropwise to a solution of 0.66 g. lithium aluminium hydride in 50 ml. anhydrous diethyl ether. After heating under reflux for 30 minutes, working up is carried out in the usual way to give 7.7 g. 3-(2-pentadecylthioethylthio)-propanol in the form of a thin layer chromatographically uniform product; m.p. 53°–55° C.

EXAMPLE 24

3[(3-Octadecylthiopropoxy)-phosphoryloxy-hydroxy]-propyltrimethyl-ammonium hydroxide A mixture of 1 g. phosphoric acid 3-bromopropyl ester dichloride, 1 g. 3-octadecylthiopropanol and 1.4 ml. triethylamine in 20 ml. anhydrous methylene chloride is stirred for 30 minutes at -5° C. and in an ice-bath for 1 hour. The reaction mixture is then left to stand overnight at ambient temperature, hydrolysed by adding 20 ml. 0.1 N aqueous potassium chloride solution and stirring for 4 hours at 40° C. and then 40 ml. methanol are added thereto. After acidifying with concentrated hydrochloric acid, the organic phase is separated off and evaporated. The 1.5 g. of residue obtained is dissolved in a mixture of chloroform-methanol (1:1 v/v), gaseous trimethylamine is passed in for 1 hour and the reaction mixture is then stirred for 3 hours at 40° C. It is then evaporated and the crystals obtained are stirred with acetone, then again dissolved in 55 ml. methanol and, after adding 0.4 g. silver acetate, stirred for 3 hours at ambient temperature. After standing overnight, the reaction mixture is filtered and the filtrate evaporated, the residue of the desired product thus obtained then being purified by column chromatography in the manner described in Example 1. There is thus obtained 0.7 g. (40% of theory) of the desired product in the form of hygroscopic crystals which, according to elementary analysis, contain 4.5 mole of water; m.p. 228°–230° C. (decomp.).

EXAMPLE 25

2-Methyl-3-octadecylthiopropan-1-ol phosphoric acid monocholine ester 14.3 g. Octadecylmercaptan are added to a solution of 0.12 g. of sodium in 70 ml. methanol and then 5 g. methyl methacrylate are added dropwise, while cooling in an ice bath. After subsequently stirring for 1 hour at ambient temperature, the cold suspension is filtered with suction, washed with cold methanol and dried. There are thus obtained 16.3 g. (88% of theory) of greasy crystals of thin layer chromatographically uniform methyl $\alpha$-methyl-$\beta$-octadecylthiopropionate, reduction of which with 1.14 g. lithium aluminium hydride in 320 ml. anhydrous diethyl ether gives 14.2 g. (94% of theory) 2-methyl-3-octadecylthiopropanol; m.p. 37°–39° C.

Subsequent phosphorylation, hydrolysis and choline formation are carried out in the manner described in Example 1. The desired thin layer chromatographically uniform product is obtained in a yield of 27% of theory; m.p. 234°–238° C. It crystallises with 1.5 mole of water.

EXAMPLE 26

3-(2-Pentadecanesulphonylethylthio)-propan-1-ol phosphoric acid monocholine ester 0.7 g. Sodium are dissolved in 80 ml. methanol. 2.4 g. Mercaptoethanol and 9 g. pentadecyl bromide are then successively added thereto and the reaction mixture stirred for 3 hours at 60° C., whereafter it is taken up in diethyl ether, separated from sodium bromide and evaporated. The residue is purified by column chromatography, eluting with ligroin-diethyl ether (1:1 v/v), to give 8.9 g. (97% of theory) 2-pentadecylthioethanol; m.p. 44°–46° C.

13 g. 2-Pentadecylthioethanol are oxidised with perhydrol in 310 ml. glacial acetic acid until a uniform spot is seen in the thin layer chromatogram. There are thus obtained 11.1 g. (77% of theory) 2-pentadecanesulphonylethanol; m.p. 64°–66° C. Reaction thereof with phosphorus tribromide in diethyl ether in the presence of pyridine gives a yield of 49% of theory of 2-pentadecanesulphonylethyl bromide, which foams at 68° C. and gives a clear melt at 85° C.

Further reaction takes place analogously to Example 1, leading to the following intermediates methyl β-(2-pentadecanesulphonylethylthio)-propionate; used as crude material for the subsequent reduction; 3-(2-pentadecanesulphonylethylthio)-propanol; m.p. 73°–75° C.

The desired end product is subsequently obtained therefrom in a yield of 12% of theory. It sinters at 54° C. and at 229°–232° C. slowly decomposes with the formation of a brown coloration. It contains 2.5 mole of water.

EXAMPLE 27

3-(2-Methoxyoctadecylthio)-propan-1-ol phosphoric acid monocholine ester

This compound is obtained in a yield of 30% of theory in a manner analogous to that described in Example 1. According to the elementary analysis, it contains 2.5 mole of water. A melting point cannot be determined because of its very hygroscopic behaviour.

The starting material, 3-(2-methoxyoctadecylthio)-propanol, is a colourless oil which gradually solidifies upon standing and which can be obtained as follows:

β-Bromostearic acid (m.p. 47°–51° C.), obtained by brominating stearic acid, is esterified with methanol in the presence of a catalytic amount of p-toluenesulphonic acid. The oily ester obtained is reacted with sodium methylate to give methyl α-methoxystearate (m.p. 33°–36° C.), which is reduced with lithium aluminium hydride to give 2-methoxystearyl alcohol, the yield being 97% of theory; m.p. 36°–38° C. Reaction with phosphorus tribromide gives a yield of 20% of theory of oily 2-methoxystearyl bromide which is reacted with methyl β-mercaptopropionate to give a yield of 33% of theory of oily methyl β-(2-methoxyoctadecylthio)propionate, reduction of which with lithium aluminium hydride gives the desired propanol derivative in a yield of 94% of theory.

EXAMPLE 28

2-(3-Octadecylthiopropoxyphosphoryloxy-hydroxy)-2-methylethyl-trimethylammonium hydroxide The phosphoric ester dichloride described in Example 19 is reacted with 3-octadecylthiopropanol (preparation see Example 1) in the manner described in Example 1. The bromide of the desired compound is obtained in a yield of 50% of theory. The bromine-free compound obtained by reaction with silver acetate sinters at 61° C., liquifies at 139° C. and decomposes at 200° C.

EXAMPLE 29

2-Methyl-3-octadecanesulphonylpropan-1-ol phosphoric acid monocholine ester

Oxidation of the compound described in Example 25 with 30% hydrogen peroxide in glacial acetic acid gives a yield of 49% of theory of the desired sulphone which sinters at 59° C. and decomposes at 227°–234° C.

EXAMPLE 30

3-Tetradecylthiopropan-1-ol phosphoric acid monocholine ester 10 g. 1-Bromotetradecane and 4 ml. methyl β-mercaptopropionate are stirred under reflux for 4 hours in a solution of 0.83 g. sodium in 110 ml. methanol. The reaction mixture is then evaporated in a vacuum and the residue is taken up in ligroin, filtered and the filtrate evaporated. The residue (11 g.; m.p. 32° C.) is dissolved in 55 ml. anhydrous diethyl ether and rapidly added dropwise to a solution of 0.94 g. lithium aluminium hydride in 110 ml. anhydrous diethyl ether. After refluxing for 30 minutes, no starting material can be detected in the thin layer chromatogram. After working up in the usual way, there are obtained 9.45 g. 3-tetradecylthiopropanol (m.p. 34°–38° C.) which is further worked up analogously to the method described in Example 1 to give 1.9 g. (58% of theory) of the desired end product in the form of a monohydrate which sinters at 63° C. and decomposes at 231°–233° C.

EXAMPLE 31

2-Methyl-3-octadecanesulphinylpropan-1-ol phosphoric acid monocholine ester

2-Methyl-3-octadecylthiopropanol, the preparation of which is described in Example 25, is oxidised in the usual way to the sulphoxide, using 30% hydrogen peroxide in glacial acetic acid. After purification on a silica gel column (elution agent chloroform-methanol 9:1 v/v), the desired intermediate compound is obtained in a yield of 55% of theory; m.p. 56°–58° C. Phosphorylation and choline ester formation are then carried out in the manner described in Example 1. After the usual purification, the desired compound is obtained in a yield of 12% of theory in the form of crystals containing 1.5 mole of water. The decomposition point thereof is 235°–240° C.

EXAMPLE 32

N-[2-(3-Hexadecylthiopropoxyphosphoryloxy-hydroxy)ethyl]-N,N-diethylamine

A. In a manner analogous to that described in Example 6 but using diethylamine instead of trimethylamine, the desired compound is obtained in a yield of 15% of theory. It sinters at 66° C. and gives a clear melt at 104°–110° C. It crystallises with 0.5 mole of water.

B. When using a 33% solution of dimethylamine in ethanol, there is obtained, in a yield of 9% of theory, N-[2-(3-hexadecylthiopropoxyphosphoryloxy-hydroxy)ethyl]-N,N-dimethylamine. This compound also crystallises with 0.5 mole of water, sinters at 84° C. and gives a clear melt at 145°–150° C.

C. When using a 33% solution of methylamine in ethanol, there is obtained, in a yield of 19% of theory, N-[2-(3-hexadecylthiopropoxyphosphoryloxyhydroxy)-ethyl]-N-methylamine. The compound sinters at 91° C. and, upon further heating, gives a clear melt at 194° C.

D. Finally, when using a concentrated aqueous solution of ammonia, there is obtained, in a yield of 11% of theory, 2-(3-hexadecylthiopropoxyphosphoryloxyhydroxy)-ethylamine. The compound sinters at 170° C., begins to melt at 195° C. and at 218° C. a brown melt is obtained. The compound crystallises with 0.5 mole of water.

EXAMPLE 33

3-Hexadecylthio-2-methylpropan-1-ol phosphoric acid monocholine ester

In a manner analogous to that described in Example 25 but using hexadecylmercaptan, the following compounds are synthesised as intermediates: methyl α-methyl-β-hexadecylthiopropionate; yellow oil; yield 79% of theory;

2-methyl-3-hexadecylthiopropanol; white viscous mass; yield 99% of theory.

The monohydrate of the desired end product sinters at 60° C. and slowly decomposes at 229°–235° C.

EXAMPLE 34

2,2-Dimethyl-3-hexadecylthiopropan-1-ol phosphoric acid monocholine ester

Starting from 2,2-dimethylpropane-1,3-diol, in a manner analogous to that described in Example 20A, there is obtained the corresponding monobenzenesulphonate in the form of a colourless oil in a yield of 56% of theory.

In a manner analogous to that described in Example 20B, by reaction of this monobenzenesulphonate with hexadecylmercaptan there is obtained 2,2-dimethyl-3-hexadecylthiopropanol in a yield of 16% of theory; m.p. 25°–28° C.

This propanol derivative is then phosphorylated in a manner analogous to that described in Example 20C, followed by reaction with trimethylamine, to give the desired product in a yield of 34% of theory. It contains 1.5 mole of water, sinters at 70° C., begins to melt at 228° C. and decomposes at 235°–238° C.

EXAMPLE 35

Cis- and trans-3-Octadecylthiocyclohexan-1-ol phosphoric acid monocholine ester

Starting from a cis-trans mixture of cyclohexane-1,3-diol, by reacting with benzenesulphochloride in the manner described in Example 20A, there is obtained the the corresponding monobenzenesulphonate, in the form of an oily cis-trans mixture, in a yield of 62% of theory.

Reaction thereof with octadecylmercaptan analogously to Example 20B, followed by separation of the isomeric mixture on a silica gel column, using diethyl ether-ligroin (1:4 v/v) as elution agent, gives the two 3-octadecylthiocyclohexanols, each in a yield of 12% of theory.

On the basis of NMR spectroscopic investigations, the compound melting at 50°–52° C. is the cis compound (both substituents in the 1,3-position in the equatorial position) and the other fraction melting at 44°–46° C. is the trans compound.

Both compounds are then phosphorylated in the usual way and then reacted with trimethylamine. The desired end product obtained from the cis compound sinters at 51° C. and melts with decomposition at 241°–244° C. and the desired end product obtained from the trans compound sinters at 45° C. and melts with decomposition at 239°–241° C.

According to the elementary analysis (determination of C, H, N, P and S) both products contain 1.5 mole of water.

EXAMPLE 36

3-(14-Methoxytetradecylthio)-propan-1-ol phosphoric acid monocholine ester 1,14-Dibromotetradecane (m.p. 38°–40° C. ) is obtained in a yield of 92% of theory from the corresponding diol (see Helv. Chim. Acta, 9, 271/1926) in a manner analogous to that described in Org. Synth., Coll. Vol. I, 29.

3.6 g. of the dibromo compound are added to a solution of 0.23 g. sodium in a mixture of 40 ml. methanol and 1.1 ml. methyl β-mercaptopropionate and the suspension stirred under reflux for 4 hours. The reaction mixture is then evaporated, the residue is stirred with diethyl ether and the ethereal solution is separated off, evaporated and the residue is chromatographed on a silica gel column with diethyl ether-ligroin (1:10 v/v). The desired fractions are combined and, after evaporation, give 1.6 g. (41% of theory) methyl β-(14-bromotetradecylthio)-propionate; m.p. 33°–35° C.

This compound is then boiled for 15 hours in a sodium methylate solution to give a yield of 11% of theory of methyl β-(14-methoxytetradecylthio)-propionate, which must also be purified by column chromatography; m.p. 31°–32° C.

0.8 g. of this methoxy compound is reduced with 62 mg. lithium aluminium hydride in 25 ml. anhydrous diethyl ether to give 0.6 g (86% of theory) 3-(14-methoxytetradecylthio)-propanol; m.p. 35°–37° C.

In a manner analogous to that described in Example 20C, this compound is then phosphorylated and reacted to give the choline ester. There is thus obtained a yield of 26% of theory of the desired compound in the form of a monohydrate which sinters at 76° C. and melts with decomposition at 238°–244° C.

EXAMPLE 37

N-[2-(3-Hexadecylthiopropoxyphosphoryloxy-hydroxy)ethyl]-N-methyl-N,N-diethylammonium hydroxide 3.7 g. of the compound prepared according to Example 32A are stirred for 2 hours at ambient temperature in 37 ml. tetrahydrofuran, together with 4.2 g. sodium bicarbonate in 50 ml. water and 8.5 ml. methyl iodide. Thereafter, the starting material spot has disappeared from the thin layer chromatogram and a new main spot appears. After evaporation in a vacuum, the residue is taken up in chloroform, filtered and evaporated and the base prepared by the action of silver acetate in methanol and then purified by column chromatography in the manner described in Example 1. The yield is 13% of theory. The compound, which contains 4.5 mole of water, sinters at 40° C. and decomposes at 119° C.

EXAMPLE 38

2-Isopropyl-3-octadecylthiopropan-1-ol phosphoric acid monocholine ester 10.1 g. Diethyl isopropylmalonate are reduced in the usual way with 2.7 g. lithium aluminium hydride in 150 ml. anhydrous diethyl ether to give 5.9 g. of an oil which is thin layer chromatographically uniform.

In a manner analogous to that described in Example 20A, this compound is reacted with benzenesulphochloride to give the monobenzenesulphonate of 2-isopropylpropane-1,3-diol in the form of a colourless oil in a yield of 42% of theory.

From this diol, in a manner analogous to that described in Example 20B, there is obtained, in a yield of 87% of theory, 2-isopropyl-3-octadecylthiopropanol; m.p. 29° C.

Thereafter, this is phosphorylated in the manner described in Example 20C and further reacted with trimethylamine to give the desired end product in the form of crystals in a yield of 37% of theory. It contains 1.5 mole of water, sinters at 55° C. and melts with decomposition at 230°–233° C.

EXAMPLE 39

4-Heptadecylthio-3-methyl-n-butan-2-ol phosphoric acid monocholine ester

In a manner analogous to that described hereinbefore, there is obtained the benzenesulphonate of 1-hydroxy-2-methyl-butan-3-one in a yield of 30% of theory in the form of an oil. Reaction thereof with heptadecylmercaptan gives, after column chromatographic purification, a yield of 61% of theory of 1-heptadecylthio-2-methylbutan-3-one in the form of an oil. Subsequent reduction with lithium aluminium hydride gives a yield of 85% of theory of thin layer chromatographically uniform 1,2-dimethyl-3-heptadecylthiopropanol; m.p. 28°-30° C. Phosphorylation and choline ester formation are carried out in the manner described in Example 20C to give the desired compound in a yield of 13% of theory. It crystallises with 1.5 mole of water, sinters at 55° C. and melts with decomposition at 230°-233° C.

EXAMPLE 40

3-Octadecylthiobutan-1-ol phosphoric acid monocholine ester 2 g. 3-Octadecylthiobutanol (m.p. 35°-38° C. ) is phosphorylated and reacted to give the choline ester (1.85 g.; 59% of theory) in the manner described in Example 20C. Purification on a silica gel column gives crystals which sinter at 58° C., become discoloured above 208° C. and decompose at 232° C. The compound crystallises with 1.5 mole of water.

The starting material is obtained as follows: Butylene-1,3-glycol is reacted with acetic anhydride at ambient temperature to give butane-1,3-diol 1-acetate in a yield of 63% of theory. It is then esterified with benzenesulphochloride in the presence of pyridine and the reaction product is eluted over a silica gel column with diethyl ether-ligroin (1:1 v/v). There is obtained a yield of 24% of theory of a colourless oil which is reacted with sodium octadecanethiol in the manner described in Example 20B and then treated with a dilute aqueous solution of sodium hydroxide to give a yield of 12% of theory of 3-octadecylthiobutanol; m.p. 35°-38° C.

EXAMPLE 41

3-(9-Octyloxynonylthio)-propan-1-ol phosohoric acid monocholine ester 3-(9-Octyloxynonylthio)-propanol (m.p. 29°-32° C.) is phosphorylated analogously to Example 20C and, after further working up in the manner there described, gives a yield of 39% of theory of the desired choline ester which crystallises with 1.75 mole of water. The compound sinters at 50° C. and, upon further heating, decomposes at 221°-224° C.

EXAMPLE 42

3-(4-Tridecyloxybutylthio)-propan-1-ol phosphoric acid monocholine ester 2.3 g. Sodium are dissolved by warming in 44 ml. butane-1,4-diol, 38 ml. 1-bromotridecane are added thereto and the reaction mixture is stirred for 5 hours at a bath temperature of 150° C. After cooling, extraction is carried out with a mixture of diethyl ether-ligroin (1:2 v/v), the extract is evaporated and the residue is purified on a silica gel column by elution with ligroin which is subsequently replaced by diethyl ether-ligroin (1:1 v/v). The desired fractions are collected and evaporated. 19.4 g. (71% of theory) of thin layer chromatographically uniform 4-tridecyloxybutanol are thus obtained; m.p. 26°-29° C.

10 g. of this butanol derivative are dissolved in 100 ml. diethyl ether, 0.6 ml. pyridine is added thereto and 1.4 ml. phosphorus tribromide is added dropwise, while cooling in an ice bath. After standing overnight at ambient temperature, the reaction mixture is diluted with diethyl ether, shaken up with ice water and the ether extract separated off, dried and evaporated. The residue of 9.2 g. of a yellowish oil is eluted through a silica gel column with diethyl ether-ligroin (1:1 v/v). The uniform fractions are combined and evaporated to give 5.5 g. (45% of theory) of thin layer chromatographically uniform 4-tridecyloxybutyl bromide in the form of a yellowish oil.

This bromide is stirred for 3 hours under reflux with 1.9 g. methyl β-mercaptopropionate in 75 ml. methanol which contains 378 mg. sodium. The solution is then evaporated and the residue again purified by column chromatography, eluting with diethyl ether-ligroin (1:10 v/v). There are thus obtained 5.7 g. (93% of theory) methyl β-(4-tridecyloxybutylthio)-propionate in the form of a yellowish oil.

This ester is reduced in 70 ml. diethyl ether with 0.4 g. lithium aluminium hydride. After stirring for 1 hour under reflux, decomposition is carried out in the usual way, and the residue obtained after evaporating the diethyl ether is eluted through a silica gel column with diethyl ether-ligroin (1:1 v/v) to give 4 g. (77% of theory) of thin layer chromatographically uniform 3-(4-tridecyloxybutylthio)-propanol; m.p. 32°-34° C.

The reaction to give the desired end product is carried out analogously to the method described in Example 20C. There are obtained 2.1 g. (33% of theory) of the desired end product which crystallises with 2.5 mole of water, sinters at 55° C. and decomposes at 218° C.

EXAMPLE 43

3-Pentadecylthiopropan-1-ol phosphoric acid monocholine ester

1-Bromopentadecane is reacted in the usual way with ethyl β-mercaptopropionate and the syrup obtained reduced with lithium aluminium hydride to give a yield of 84% of theory of 3-pentadecylthiopropanol; m.p. 36°-39° C.

The further reaction steps, carried out analogously to Example 20C, give a yield of 61% of theory of the desired end product which sinters at 60° C. and decomposes at 237° C. It crystallises with 1.25 mole of water.

EXAMPLE 44

5-Hexadecylthiopentan-1-ol phosphoric acid monocholine ester

5-Hexadecylthiopentanol (m.p. 40°-43° C.; obtained in a yield of 63% of theory from pentane-1,5-diol via the oily monobenzenesulphonate with potassium hexadecylmercaptan) is phosphorylated in the usual way (see Example 20C) and then reacted to give the choline ester in a yield of 41% of theory. The water-soluble crystals obtained sinter at 58° C. and decompose at 228°-230° C. The product crystallises with 1.5 mole of water.

EXAMPLE 45

3-(10-n-Butoxydecyloxyethylthio)-propan-1-ol phosphoric acid monocholine ester 3-(10-n-Butoxydecyloxyethylthio)-propanol (m.p. 23°–27° C.) is phosphorylated and reacted to give the choline ester in the manner described in Example 20C. The desired end product is obtained in a yield of 35% of theory in the form of water-soluble crystals which sinter at 36° C. and decompose at 227°–229° C. The hygroscopic crystals are present in the form of a dihydrate.

The starting material is obtained as follows:

Monosodium decane-1,10-diol is reacted with n-butyl bromide to give oily 10-n-butoxydecanol in a yield of 62% of theory. This is brominated with phosphorus tribromide in the presence of pyridine to give an oily product in a yield of 37% of theory. After reaction of this 10-n-butoxydecyl bromide with monosodium ethylene glycol, there is obtained oily 10-n-butoxydecyloxyethanol in a yield of 36% of theory, which is reacted with phosphorus tribromide in the presence of pyridine to give oily 10-n-butoxydecyloxyethyl bromide in a yield of 52% of theory. This is then reacted with methyl β-mercaptopropionate in the presence of sodium methylate to give a yield of 49% of theory of oily methyl β-(10-n-butoxydecyloxyethylthio)-propionate, reduction of which with lithium aluminium hydride gives a yield of 90% of theory of 3-(10-n-butoxydecyloxyethylthio]-propanol; m.p, 23°–27° C.

EXAMPLE 46

3-(11-Hexyloxyundecylthio)-propan-1-ol phosphoric acid monocholine ester

11-Bromoundecan-1-ol (m.p. 45°–48° C.) is reacted with sodium hexanolate and the syrupy product obtained is reacted with phosphorus tribromide in the presence of pyridine. The structure of the oil obtained is confirmed by mass spectroscopy as being 11-bromoundecyloxyhexane. This bromo compound is reacted with methyl β-mercaptopropionate in sodium methylate solution and the oil obtained is then reduced with lithium aluminium hydride to give 3-(11-hexyloxyundecylthio)-propanol; m.p. 27°–29° C. Phosphorylation and choline ester formation in a manner analogous to that described in Example 20C gives the desired end product in a yield of 55% of theory in the form of a monohydrate which sinters at 98° C. and decomposes at 226°–229° C.

EXAMPLE 47

3-(7-Decyloxyheptylthio)-propan-1-ol phosphoric acid monocholine ester 3-(7-Decyloxyheptylthio)-propanol (m.p. 28°–32° C.), obtained by reacting heptane-1,7-diol with 1-bromodecane to give 7-decyloxyheptanol, bromination thereof to give 7-decyloxyheptyl bromide, reaction with methyl β-mercaptopropionate to give methyl β-(7-decyloxyheptylthio)-propionate and reduction with lithium aluminium hydride, is reacted in the manner described in Example 20C to give the desired choline ester in a yield of 17% of theory. The water-soluble, white crystals sinter at 53° C. and melt at 224° C.

In an analogous manner, from 3-(3-tetradecyloxypropylthio)-propanol (m.p. 38°–41° C.; prepared from methyl β-mercaptopropionate and 1-bromo-3-tetradecylpropane in sodium methylate solution and subsequent reduction with lithium aluminium hydride) there is obtained a yield of 38% of theory of 3-(3-tetradecyloxypropylthio)-propan-1-ol phosphoric acid monocholine ester which sinters at 52° C. and decomposes at 230°–233° C.

EXAMPLE 48

In a manner analogous to that of Example 20C, by the reaction of 3-hexadecylthio-2-methoxypropan-1-ol (wax-like substance) with 2-bromoethyl phosphoric acid ester dichloride, subsequent saponification, treatment with trimethylamine and silver acetate, there is obtained 3-hexadecylamino-2-methoxypropan-1-ol phosphoric acid monocholine ester (m.p. 255°–256° C.) in a yield of 16% of theory. The compound contains 1 mole of water of crystallisation The hexadecylthio-2-methoxypropan-1-ol used as starting material is obtained by reacting 2-methoxypropane-1,3-diol monobenzenesulphonate (oily substance) with the sodium salt of hexadecylmercaptan.

EXAMPLE 49

Analogously to Example 48 but using 3-heptadecylthio-2-methoxypropan-1-ol (wax-like substance) as starting material, there is obtained 3-heptadecylthio-2-methoxypropan-1-ol phosphoric acid monocholine ester (m.p. 255°–257° C.) in a yield of 11% of theory. The compound contains 2 moles of water of crystallisation.

The 3-heptadecylthio-2-methoxypropan-1-ol used as starting material is obtained by reacting 2-methoxypropane-1,3-diol monobenzenesulphonate with the sodium salt of heptadecylmercaptan.

EXAMPLE 50

Analogously to Example 48 but using 2-ethoxy-3-heptadecylthiopropan-1-ol (wax-like substance m.p. <50° C.) as starting material, there is obtained 2-ethoxy-3-heptadecylthiopropan-1-ol phosphoric acid monocholine ester (m.p. 225°–230° C.) in a yield of 18% of theory. The compound contains 2 moles of water of crystallisation.

The 2-ethoxy-3-heptadecylthiopropan-1-ol used as starting material is obtained by reacting 2-ethoxypropane-3-diol monobenzenesulphonate (oily substance) with the potassium salt of heptadecylmercaptan.

EXAMPLE 51

Analogously to Example 48 but using 2-methoxy-3-(trans-octadec-9-enylthio)-propan-1-ol (wax-like substance) as starting material, there is obtained 2-methoxy-3-(trans-octadec-9-enylthio)-propan-1-ol phosphoric acid monocholine ester (wax) in a yield of 12% of theory. The compound contains 3 moles of water of crystallisation.

The 2-methoxy-3-(trans-octadec-9-enylthio)-propan-1-ol used as starting material is obtained by reacting 2-methoxy-propane-1,3-diol monobenzenesulphonate with the sodium salt of trans-octadec-9-enylmercaptan.

EXAMPLE 52

Analogously to Example 48 but using 2-methoxy-3-(octadec-9,12-dienylthio)-propan-1-ol (wax-like substance) as starting material, there is obtained 2-methoxy-3-(octadec-9,12-dienylthio)-propan-1-ol phosphoric acid monocholine ester (wax) in a yield of 11% of theory. The compound contains 3 moles of water of crystallisation.

The 2-methoxy-3-(octadec-9,12-dienylthio)-propan-1-ol used as starting material is obtained by reacting 2-methoxy-propane-1,3-diol monobenzenesulphonate with the sodium salt of octadec-9,12-dienylmercaptan.

EXAMPLE 53

Analogously to Example 48 but using 2-methoxy-3-(1-methyl-octadecylthio)-propan-1-ol (wax-like substance) as starting material, there is obtained 2-methoxy-3-(1-methyloctadecylthio)-propan-1-ol phosphoric acid monocholine ester (m.p. 256°–258° C.) in a yield of 34% of theory. The compound contains 2 moles of water of crystallisation.

The 2-methoxy-3-(1-methyloctadecylthio)-propan-1-ol used as starting material is obtained by reacting 2-methoxy-propane-1,3-diol monobenzenesulphonate with the potassium salt of 1-methyloctadecylmercaptan.

EXAMPLE 54

Analogously to Example 48 but using 3-(3-heptyldecylthio)-2-methoxypropan-1-ol (wax-like substance) as starting material, there is obtained 3-(3-heptyldecylthio)-2-methoxypropan-1-ol phosphoric acid monocholine ester (wax) in a yield of 48% of theory. The compound contains 1 mole of water of crystallisation.

The 3-(3-heptyldecylthio)-2-methoxypropan-1-ol used as starting material is obtained by reacting 2-methoxypropane-1,3-diol monobenzenesulphonate with the potassium salt of 3-heptyldecylmercaptan.

EXAMPLE 55

Analogously to Example 48 but using 2-methoxy-3-(3-tetradecyloxypropylthio)-propan-1-ol (wax-like substance) as starting material, there is obtained 2-methoxy-3-(3-tetradecyloxypropylthio)-propan-1-ol phosphoric acid monocholine ester (m.p. 242°–244° C.) in a yield of 18% of theory. The compound contains 2 mole of water of crystallisation.

The 2-methoxy-3-(3-tetradecyloxypropylthio)-propan-1-ol used as starting material is obtained by reacting 2-methoxypropane-1,3-diol monobenzenesulphonate with the potassium salt of 3-tetradecyloxypropylmercaptan.

EXAMPLE 56

Analogously to Example 48 but using 3-(5-dodecyloxypentylthio)-2-methoxypropan-1-ol as starting material, there is obtained 3-(5-dodecyloxypentylthio)-2-methoxypropan-1-ol phosphoric acid monocholine ester (m.p. 245°–247° C. in a yield of 25% of theory. The compound contains 2 mole of water of crystallisation.

The 3-(5-dodecyloxypentylthio)-2-methoxypropan-1-ol used as starting material is obtained by reacting 2-methoxypropane-1,3-diol monobenzenesulphonate with the potassium salt of 5-dodecyloxypentylmercaptan.

EXAMPLE 57

Analogously to Example 48 but using 2-methoxy-3-(8-nonyloxyoctylthio)-propan-1-ol (wax-like substance) as starting material, there is obtained 2-methoxy-3-(8-nonyloxyoctylthio)-propan-1-ol phosphoric acid monocholine ester (wax) in a yield of 20% of theory. The compound contains 1 mole of water of crystallisation.

The 2-methoxy-3-(8-nonyloxyoctylthio)-propan-1-ol used as starting material is obtained by reacting 2-methoxypropane-1,3-diol monobenzenesulphonate with the potassium salt of 8-nonyloxyoctylmercaptan.

EXAMPLE 58

Analogously to Example 48 but using 2-ethyl-3-hexadecylthiopropan-1-ol (wax-like substance) as starting material, there is obtained 2-ethyl-3-hexadecylthiopropan-1-ol phosphoric acid monocholine ester (m.p. 236°–238° C.) in a yield of 41% of theory. The compound contains 2 moles of water of crystallisation.

The 2-ethyl-3-hexadecylthiopropan-1-ol used as starting material is obtained by reacting 2-ethylpropane-1,3-diol monobenzene sulphonate with the sodium salt of hexadecylmercaptan.

EXAMPLE 59

Analogously to Example 48 but using 3-hexadecylthio-2-propylpropan-1-ol (wax-like substance) as starting material, there is obtained 3-hexadecylthio-2-propylpropan-1-ol phosphoric acid monocholine ester (m.p. 239°–242° C.) in a yield of 13% of theory. The compound contains 2 moles of water of crystallisation.

The hexadecylthio-2-propylpropan-1-ol used as starting material is obtained by reacting 2-propylpropane-1,3-diol monobenzenesulphonate (oily substance) with the sodium salt of hexadecylmercaptan.

EXAMPLE 60

Analogously to Example 48 but using 2-n-butyl-3-octadecylthiopropan-1-ol (wax-like substance; m.p. 36°–40° C.) as starting material, there is obtained 2-n-butyl-3-octadecylthiopropan-1-ol phosphoric acid monocholine ester (m.p. 232°–238° C.) in a yield of 17% of theory. The compound contains 4 moles of water of crystallisation.

The 2-n-butyl-3-octadecylthiopropan-1-ol used as starting material is obtained by reacting 2-n-butylpropane-1,3-diol monobenzenesulphonate (oily substance) with the sodium salt of octadecylmercaptan.

EXAMPLE 61

Analogously to Example 48 but using 2-benzyloxy-3-octadecylthiopropan-1-ol (wax-like substance; m.p. 39°–42° C.) as starting material, there is obtained 2-benzyloxy-3-octadecylthiopropan-1-ol phosphoric acid monocholine ester (m.p. 210°–212° C.) in a yield of 28% of theory. The compound contains 1 mole of water of crystallisation.

The 2-benzyloxy-3-octadecylthiopropan-1-ol used as starting material is obtained by reacting 2-benzyloxypropane-1,3-diol monobenzenesulphonate (oily substance) with the sodium salt of octadecylmercaptan.

EXAMPLE 62

Analogously to Example 48 but using 3-hexadecylthio-2-methoxymethylpropan-1-ol (wax-like substance) as starting material, there is obtained 3-hexadecylthio-2-methoxymethylpropan-1-ol phosphoric acid monocholine ester (m.p. 243°–245° C.) in a yield of 22% of theory. The compound contains 3 moles of water of crystallisation.

The 3-hexadecylthio-2-methoxymethylpropan-1-ol used as starting material is obtained by reacting 2-methoxymethylpropane-1,3-diol monobenzenesulphonate (oily substance) with the sodium salt of hexadecylmercaptan.

EXAMPLE 63

Analogously to Example 48 but using 2-ethoxymethyl-3-hexadecylthiopropan-1-ol (wax-like substance) as starting material, there is obtained 2-ethoxymethyl-3-hexadecylthiopropan-1-ol phosphoric acid monocholine ester (m.p. 243°–246° C.) in a yield of 11% of theory. The compound contains 2.5 mole of water of crystallisation.

The 2-ethoxymethyl-3-hexadecylthiopropan-1-ol used as starting material is obtained by reacting 2-ethoxymethylpropane-1,3-diol monobenzenesulphonate (oily substance) with the sodium salt of hexadecylmercaptan.

EXAMPLE 64

Analogously to Example 48 but using 2,2-bis-(methoxymethyl)-3-octadecylthiopropan-1-ol (wax-like substance) as starting material, there is obtained 2,2-bis-(methoxymethyl)-3-octadecylthiopropan-1-ol phosphoric acid monocholine ester (m.p. 237°–239° C.) in a yield of 26% of theory. The compound contains 1 mole of water of crystallisation.

The 2,2-bis-(methoxymethyl)-3-octadecylthiopropan-1-ol used as starting material is obtained by reacting 2,2-bis-(methoxymethyl)-propane-1,3-diol monobenzenesulphonate (oily substance) with the sodium salt of octadecylmercaptan.

EXAMPLE 65

Analogously to Example 48 but using 3-heptadecylthio-2-methoxy-2-methylpropan-1-ol (wax-like substance) as starting material, there is obtained 3-heptadecylthio-2-methoxy-2-methylpropan-1-ol phosphoric acid monocholine ester (m.p. 244°–251° C.) in a yield of 19% of theory. The compound contains 2 moles of water of crystallisation.

The 3-heptadecylthio-2-methoxy-2-methylpropan-1-ol used as starting material is obtained by reacting methyl 2-methylglycidate with the sodium salt of heptadecylmercaptan to give methyl 3-heptadecylthio-2-hydroxy-2-methylpropionate (m.p. 42°–45° C.), subsequent methylation with methyl iodide to give methyl 3-heptadecylthio-2-methoxy-2-methylpropionate (oily substance) and reduction with lithium aluminium hydride.

EXAMPLE 66

Analogously to Example 48 but using 4-hexadecylthio-butan-2-ol (wax-like substance) as starting material, there is obtained 4-hexadecylthiobutan-2-ol phosphoric acid monocholine ester (wax) in a yield of 19% of theory. The compound contains 2.5 mole of water of crystallisation.

The 4-hexadecylthiobutan-2-ol used as starting material is obtained by reducing 4-hexadecylthiobutan-2-one (m.p. 45°–47° C.) with lithium aluminium hydride.

EXAMPLE 67

Analogously to Example 48 but using 4-octadecylthiopentan-2-ol (wax-like substance) as starting material, there is obtained 4-octadecylthiopentan-2-ol phosphoric acid monocholine ester (m.p. 239°–245° C.) in a yield of 7% of theory. The compound contains 3 mole of water of crystallisation.

The 4-octadecylthiopentan-2-ol used as starting material is obtained by reacting pentane-2,4-diol monobenzenesulphonate (oily substance) with the sodium salt of octadecylmercaptan.

EXAMPLE 68

Analogously to Example 48 but using 3-hexadecylthiocyclopentan-1-ol (wax-like substance; m.p. 45°–50° C.) as starting material, there is obtained 3-hexadecylthiocyclopentan-1-ol phosphoric acid monocholine ester (m.p. 253°–256° C.) in a yield of 33% of theory. The compound contains 2 moles of water of crystallisation.

The hexadecylthiocyclopentan-1-ol used as starting material is obtained by reacting cyclopentane-1,3-diol monobenzenesulphonate (oily substance) with the sodium salt of hexadecylmercaptan.

EXAMPLE 69

Analogously to Example 48 but using (S)-2-methanesulphonamido-3-octadecylthiopropan-1-ol (m.p. 85°–87° C.) as starting material, there is obtained (S)-2-methanesulphonamido-3-octadecylthiopropan-1-ol phosphoric acid monocholine ester (m.p. 212°–215° C., decomp.) in a yield of 14% of theory. The compound contains 1 mole of water of crystallisation.

The (S)-2-methanesulphonamido-3-octadecylthiopropan-1-ol used as starting material is obtained by reacting (L)-S-octadecylcysteine ethyl ester with methanesulphochloride to give (L)-N-methanesulphonyl-S-octadecylcysteine ethyl ester (m.p. 63°–65° C.) and subsequent reduction with lithium aluminium hydride.

EXAMPLE 70

Analogously to Example 48 but using 3-hexadecylthio-2-methoxymethylpropane-1-thiol (oil) as starting material, there is obtained thiophosphoric acid 0-choline ester S-(3-hexadecylthio-2-methoxymethylpropyl) ester (m.p. 230°–235° C.; decomp.) in a yield of 14% of theory. The compound contains 3 moles of water of crystallisation.

The 3-hexadecylthio-2-methoxymethylpropane-1-thiol used as starting material is obtained by reacting 3-hexadecylthio-2-methoxymethylpropan-1-ol with benzenesulphochloride to give 3-hexadecylthio-2-methoxymethylpropane-1-ol (oily substance), reaction thereof with thiourea to give the corresponding isothiuronium salt, subsequent hydrolysis with 10N aqueous potassium hydroxide solution and acidification with hydrochloric acid.

EXAMPLE 71

Analogously to Example 48 but using 3-[2-(N-dodecylcarboxamido)-ethylthio]-2-methoxypropan-1-ol (m.p. 67°–69° C. ) as starting material, there is obtained 3-[2-(N-dodecylcarboxamido)-ethylthio]-2-methoxypropan-1-ol phosphoric acid monocholine ester (wax-like substance) in a yield of 16% of theory. The compound contains 4 moles of water of crystallisation.

The 3-[2-(-N-dodecylcarboxamido)-ethylthio]-2-methoxypropan-1-ol used as starting material is obtained by reacting 2-methoxypropane-1,3-diol monobenzenesulphonate with the sodium salt of 2-(N-dodecylcarboxamido)-ethylmercaptan, this mercaptan being obtained by reacting ethyl 3-mercaptopropionate with dodecylamine.

EXAMPLE 72

Analogously to Example 48 but using 2-methoxy-3-(9-phenyloctadecylthio)-propan-1-ol (oily substance) as starting material, there is obtained 2-methoxy-3-(9-phenyloctadecylthio)-propan-1-ol phosphoric acid monocholine ester (wax-like substance) in a yield of 10% of theory. The compound contains 2 moles of water of crystallisation.

The 2-methoxy-3-(9-phenyloctadecylthio)-propan-1-ol used as starting material is obtained by reacting 2- methoxypropane-1,3-diol monobenzenesulphonate with the sodium salt of 9-phenyloctadecylmercaptan.

EXAMPLE 73

Analogously to Example 48 but using 3-[11-(N-n-butylcarboxamido)-undecylthio]-2-methoxypropan-1-ol (m.p. 62°–64° C.) as starting material, there is obtained 3-[11-(N-n-butylcarboxamido)-undecylthio]-2-methoxypropan-1-ol phosphoric acid monocholine ester (wax-like substance) in a yield of 13% of theory. The compound contains 3.5 mole of water of crystallisation.

The 3-[11-(-N-n-butylcarboxamido)-undecylthio]-2-methoxypropan-1-ol used as starting material is obtained by reacting 2-methoxypropane-1,3-diol monobenzenesulphonate with the sodium salt of 11-(N-n-butylcarboxamido)-undecylmercaptan.

EXAMPLE 74

Analogously to Example 48 but using 2-methoxy-3-octadecylthiopropane-1-thiol (wax-like substance) as starting material, there is obtained thiophosphoric acid O-choline ester S-(2-methoxy-3-octadecylthiopropyl) ester (m.p. 219°–221° C., decomp.) in a yield of 7% of theory. The compound contains 4 mole of water of crystallisation.

The 2-methoxy-3-octadecylthiopropane-1-thiol used as starting material is obtained by reacting 2-methoxy-3-octadecylthiopropan-1-ol with benzenesulphochloride to give 2-methoxy-3-octadecylthiopropan-1-ol benzenesulphonate (oily substance), reacting with thiourea to give the corresponding isothiuronium salt, subsequent hydrolysis with 10N aqueous potassium hydroxide solution and acidification with hydrochloric acid.

EXAMPLE 75

Analogously to Example 48 but using 4-octadecylthiopentane-2-thiol (m.p. 38°–40° C.) as starting material, there is obtained thiophosphoric acid O-choline ester S-(4-octadecylthio-2-pentyl) ester (m.p. 244°–245° C., decomp.) in a yield of 9% of theory. The compound contains 3.5 mole of water of crystallisation.

The 4-octadecylthiopentane-2-thiol used as starting material is obtained by reacting 4-octadecylthiopentan-2-ol with benzenesulphochloride to give 4-octadecylthiopentan-2-ol benzenesulphonate (oily substance), reacting with thiourea to give the corresponding isothiuronium salt, subsequent hydrolysis with 10N aqueous potassium hydroxide solution and acidification with hydrochloric acid.

EXAMPLE 76

2-Methyl-2-methoxycarbonyl-3-hexadecylthiopropan-1-ol phosohoric acid monocholine ester Methyl 2,2-bis-(hydroxymethyl)-monobenzenesulphonate propionate (m.p. 58°–62° C.) is reacted with hexadecyl sodium mercaptide in methanol to give methyl 2-hydroxymethyl-2-hexadecylthiomethylpropionate (m.p. 25°–27° C.). Phosphorylation, hydrolysis and choline ester formation take place in a manner analogous to that described in Example 20C to give a yield of 31% of theory of the monohydrate of the desired compound, which sinters at 65° C. and decomposes at 238°–240° C.

EXAMPLE 77

Thiophosphoric acid O-choline ester S-2-methyl-3-hexadecylthiopropyl ester

From the 2-methyl-3-hexadecylthiopropanol described in Example 33 there is obtained, via its benzenesulphonate, by boiling with thiourea in ethanol, the oily 2-methyl-3-hexadecylthiopropanethiol, the phosphorylation, hydrolysis and choline ester formation of which are carried out analogously to Example 20C to give the desired end product in a yield of 17% of theory which, after sintering at 45° C., melts with foaming at 262° C. The compound is obtained as a trihydrate.

EXAMPLE 78

Analogously to Example 48 but using 3-hexadecylthio-2-(2-methoxyethoxy)-propan-1-ol (oily substance) as starting material, there is obtained 3-hexadecylthio-2-(2-methoxyethoxy)-propan-1-ol phosphoric acid monocholine ester (m.p. 257°–258° C., decomp.) in a yield of 18% of theory. The compound contains 1 mole of water of crystallisation.

The 3-hexadecylthio-2-(2-methoxyethoxy)-propan-1-ol used as starting material is obtained by reacting 2-(2-methoxyethoxy)-propane-1,3-diol monobenzenesulphonate (oily substance) with the potassium salt of hexadecylmercaptan.

EXAMPLE 79

2-Hexadecyloxy-3-methylthiopropan-1-ol phosphoric acid monocholine ester 0.95 g. Triethylamine are added at 0° C. to 0.9 g. (2.6 mMol) 2-hexadecyloxy-3-methylthiopropan-1-ol in 15 ml. anhydrous toluene, followed by the dropwise addition of a solution of 0.95 g. (3.6 mMol) 2-bromoethylphosphoric acid ester dichloride in 15 ml. anhydrous toluene. The reaction mixture is stirred for 5 hours at 0° C. and then stirred overnight at 20° C. The reaction mixture is again cooled to 0° C. and 11 ml. 0.1N aqueous potassium chloride solution added thereto dropwise, followed by vigorous stirring for 1 hour at 0° C. and for 2 hours at 20° C., whereafter the phases are separated and the organic phase is dried and evaporated. The oily residue is dissolved in 30 ml. anhydrous chloroform/30 ml. anhydrous methanol, dry trimethylamine is passed in for 10 minutes and the reaction mixture then boiled under reflux for 24 hours. The solvent is stripped off and the residue is dissolved in 50 ml. anhydrous methanol and mixed with 1 g. silver acetate. The reaction mixture is stirred for 2 hours at ambient temperature, filtered with suction and the filtrate is evaporated. The oily residue is purified over 100 g. of silica gel (elution agent methylene chloride-methanol-water 65/25/4 v/v/v). After stripping off the elution agent and drying, the product is reprecipitated from chloroform/acetone. There is obtained 0.24 g. (about 18% of theory) of the desired end product in the form of an amorphous, chromatographically uniform product.

The 2-hexadecyloxy-3-methylthiopropan-1-ol used as starting material is new and is prepared in the following manner:

1-Thioglycerol is methylated with methyl iodide to give 3-methylthiopropane-1,2-diol and subsequently reacted with sodium hydride and 1-bromohexadecane to give a mixture of the two isomeric hexadecyl ethers, which are separated by column chromatography (wax-like substances).

EXAMPLE 80

Analogously to Example 79, by the reaction of 2-benzyl-3-hexadecylthiopropan-1-ol with 2-bromoethylphosphoric acid ester dichloride, subsequent saponification and reaction with trimethylamine after treatment with silver acetate, there is obtained 2-benzyl-3-hexadecylthiopropan-1-ol phosphoric acid monocholine ester. After reprecipitation from chloroform/acetone, the desired product is obtained in a yield of 13% of theory. It melts with decomposition at 220°–230° C.

The 2-benzyl-3-hexadecylthiopropan-1-ol used as starting material is new and is prepared in the following manner:

Diethyl benzylmalonate is reduced with lithium aluminium hydride to give 2-benzylpropane-1,3-diol (m.p. 64°–65° C.) and esterified with an equimolar amount of benzenesulphochloride in anhydrous pyridine to give 2-benzylpropane-1,3-diol monobenzenesulphonate (oily substance). Reaction thereof with the sodium salt of hexadecanethiol in ethanol gives the desired 2-benzyl-3-hexadecylthiopropan-1-ol (wax-like compound).

EXAMPLE 81

Analogously to Example 79, by the reaction of 3-hexadecylthio-2-phenylpropan-1-ol with 2-bromoethylphosphoric acid ester dichloride, subsequent saponification and reaction with trimethylamine after treatment with silver acetate, there is obtained 3-hexadecylthio-2-phenylpropan-1-ol phosphoric acid monocholine ester. After reprecipitation from chloroform/acetone, the desired compound is obtained in a yield of 27% of theory with a melting point of 245° C. (decomp ).

The 3-hexadecylthio-2-phenylpropan-1-ol used as starting material is new and is prepared in the following manner:

Diethyl phenylmalonate is reduced with lithium aluminium hydride to give 2-phenyl-propane-1,3-diol and esterified with an equimolar amount of benzenesulphochloride in anhydrous pyridine to give 2-phenylpropane-1,3-diol monobenzenesulphonate (wax-like substance). Reaction thereof with the potassium salt of hexadecanethiol in ethanol gives the desired 3-hexadecylthio-2-phenylpropan-1-ol (wax-like substance).

EXAMPLE 82

Analogously to Example 79, by the reaction of 2-allyl-3-hexadecylthiopropan-1-ol with 2-bromoethylphosphoric acid ester dichloride, subsequent saponification as well as reaction with trimethylamine after treatment with silver acetate gives 2-allyl-3-hexadecylthiopropan-1-ol phosphoric acid monocholine ester. After reprecipitation from chloroform/acetone, there is obtained the desired compound in a yield of 23% of theory with a melting point of 235°–238° C. (decomp.).

The 2-allyl-3-hexadecylthiopropan-1-ol used as starting material is new and is prepared in the following manner:

Diethyl allylmalonate is reduced with lithium aluminium hydride to give 2-allylpropane-1,3-diol (oil) and esterified with an equimolar amount of benzenesulphochloride in anhydrous pyridine to give 2-allylpropan-1,3-diol monobenzenesulphonate (oily substance). Reaction thereof with the sodium salt of hexadecanethiol in ethanol gives the desired 2-allyl-3-hexadecylthiopropan-1-ol (wax-like compound).

EXAMPLE 83

Analogously to Example 79, by the reaction of 2-methylene-3-octadecylthiopropan-1-ol with 2-bromoethylphosphoric acid ester dichloride, subsequent saponification, as well as reaction with trimethylamine after treatment with silver acetate gives 2-methylene-3-octadecylthiopropan-1-ol phosphoric acid monocholine ester. After reprecipitation from chloroform/acetone, there is obtained the desired compound in a yield of 18% of theory with a melting point of 235°–237° C. (decomp.).

The 2-methylene-3-octadecylthiopropan-1-ol used as starting material is new and is prepared in the following manner:

3-Bromo-2-methoxy-2-methylpropan-1-ol is reacted with the sodium salt of octadecanethiol in ethanol. The 2-methylene-3-octadecylthiopropan-1-ol (wax-like substance) is thereby obtained with the splitting off of methanol.

EXAMPLE 84

3-Tetradecylmercapto-propanol-(1)-phosphoric acid mono-choline ester

To a solution of 0.3 grams of 2-chloro- 2-oxo 1,3,2-dioxaphospholane and 0.8 ml of triethylamine in 10 ml (abs.) methylene chloride there was added dropwise at −5° to −10° C. a solution of 0.5 grams of 3-tetradecylmercapto-propanol in 10 ml (abs.) methylene chloride. The clear solution was stirred for two hours in an ice bath and left standing overnight at room temperature. The resulting mixture was concentrated and 2.5 ml of acetonitrile, containing 0.24 grams of trimethylamine, was added. The mixture was then reacted in an autoclave for 8 hours at 60° C.; the resulting compound was compared to the product of Example 30, using thin layer chromotograph, and this showed identity of the two compounds, viz., 3-tetradecylmercapto-propanol-(1)-phosphoric acid mono-choline ester. Purification was effected as set forth in Example 30.

EXAMPLE 85

+(or-)-2-Methyl-3-hexadecylmercaptopropanol-(1)-phosphoric acid monocholine ester (Enantiomer A or B)

The racemic α-methyl-β-hexadecylmercapto-propionic acid methyl ester described in Example 33 was saponified with 2 N sodium hydroxide under reflux. There was obtained racemic α-methyl-β-hexadecylmercaptopropionic acid, in 91% yield, melting point 53°–56° C.

This acid was esterified with N-hydroxysuccinimide in methylene chloride in the presence of dicyclohexacarbodiimide. The activated racemic ester, melting, point 51°–54° C., was obtained in 67% yield.

The conversion of this ester with R (+) 1-phenyl ethyl amine in methylene chlorine produced 88% of a mixture of the diastereomeric amides. These were separated in a silica gel column with acetone-toluene in a ratio of 1:30 and both pure diastereomers were obtained:

|  | Yield | M.p. | $[\alpha]_D^{20}$ c = 1, CHCl$_3$ |
|---|---|---|---|
| Diastereomer A | 17% | 88–90° C. | +42.2° |
| Diastereomer B | 17% | 71–73° C. | +33.8° |

Each diastereomeric amide was separately saponified with half concentrated sulfuric acid. One obtains, in this manner, with 60° or 63° yield, the two enantiomeric α-methyl-β-hexadecylmercapto-propionic acids (c=1, CHCl₃): M.p. 56–59 C, $[\alpha]_{578}^{20} + 9.7°$ or M.p 58°–60° C., $[\alpha]_{578}^{20} - 8.7°$.

The reduction with lithium aluminium hydride leads to the enantiomeric 2-methyl-3-hexadecylmercapto-propionols (foamy products), which as described in Example 1 were phosphorylated, hydrolyzed and, finally, reacted with trimethylamine.

After the final purification in a silica gel column one obtains the desired enantiomers:

| | Yield | Moles Water of Crystallization | M.p. | $[\alpha]_{578}^{20}$ c = 10, CHCl₃ |
|---|---|---|---|---|
| Enantiomer A | 47% | 2 | 78° C. sintered, 241–5° C. (D) | +0.9° |
| Enantiomer B | 52% | 2 | 55° C. sintered, 236–9° C. (D) | −1.2° |

The compounds of the invention possess outstanding therapeutic properties and the compounds can be administered as set forth at pages 11 et seq supra.

The compounds were tested for their cytotoxic effect on mice tumors in the following screening tests.

The target cells used were cells of a methylcholanthrene induced tumour (MethA) which is passaged in the mous as ascites and in addition Abelson-8.1-lymphoma cells (Abls) which were cultured in vitro. For the screening tests $5 \times 10^4$/ml of these cells were cultivated with different concentrations of the new sulfur-containing phospholipid compounds of the invention for 24 hours, in Dulbecco's Modified Eagle's Medium enriched with 10% heat—inactivated fetal calves serum, $5 \times 10^{-5}$ mercaptoethanol, 50 U penicillin and 50 μg streptomycin/ml. The cultivation was carried out at 37° C., 10% CO₂ in an humified incubating chamber.

The effectiveness of the test compounds was measured by comparing the growth of the tumor cells in the medium with and without the sulfur-containing phosphor lipid test compounds, i.e., a control test was run using control culture without test compound. In addition, each series of experiments included a comparison test using instead of the test compounds of the invention, 1-octadecyl-2-methyl glycero-3-phosphorylcholine (as disclosed in German Patent publication 26 19 686). The growth of the MethA cells was measured by introduction of ³H-thymidine in the DNA of the cells; the growth of the Abls cells was measured by determining the alkaline phosphatase-activity of an aliquot of the cultures. For each test substance that concentration was determined in which thymidine introduction, or alkaline phosphatase-activity, is reduced by 50% relative to the untreated tumor cell control.

In the following table the effectiveness of the substances of the invention in the above tests are set forth. The superiority of the compounds of the invention, relative to the test compounds set forth above, is expressed by a factor which is the ratio of the concentration of the comparison compound required for the 50% reduction effectiveness divided by the concentration required of the test compound for the same 50% reduction effect.

| Compound | Factor |
|---|---|
| 1-Octadecyl-2-methyl-glycero-3-phosphorylcholine | 1.0 |
| 3-Hexadecylthio-2-methyl-propan-1-ol phosphoric acid monocholine ester | 1.1 |
| 3-(4-Tridecyloxybutylthio)-propan-1-ol phosphoric acid monocholine ester | 1.4 |
| 2-Methyl-2-methoxycarbonyl-3-hexadecylthiopropan-1-ol phosphoric acid monocholine ester | 1.4 |
| 2-Methoxy-3-octadecylthiopropan 1-ol phosphoric acid monocholine ester | 1.7 |
| 2-Hexadecyloxy-3-methylthiopropan-1-ol phosphoric acid monocholine ester | 1.2 |
| 2-Methoxy-3-(3-tetradecyloxypropyl-thio)-propan-1-ol phosphoric acid monocholine ester | 1.5 |
| 3-Hexadecylthio-2-methoxymethylpropan-1-ol phosphoric acid monocholine ester | 1.5 |
| 3-Heptadecylthio-2-methoxy-2-methyl-propan-1-ol phosphoric acid monocholine ester | 1.5 |
| Thiophosphoric acid 0-choline ester S—(3-hexadecylthio-2-methoxymethyl-propyl) ester | 1.5 |
| 2-Ethoxymethyl-3-hexadecylthiopropan-1-ol phosphoric acid monocholine ester | 1.2 |

It will be understood that the specification and examples are illustrative but not limitative of the present invention and that other embodiments within the spirit and scope of the invention will suggest themselves to those skilled in the art.

What is claimed is:

1. Alkanol phosphoric acid monoammonium alkyl ester compound of the formula

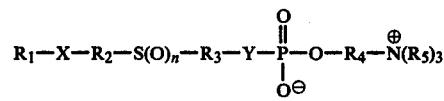

wherein
X is a valency bond, oxygen or sulfur,
Y is oxygen or sulfur,
R₁ is hydrogen, straight-chain or branched, saturated or unsaturated aliphatic hydrocarbon chain containing up to 18 carbon atoms,
R₂ is a straight-chained or branched, saturated or unsaturated aliphatic hydrocarbon chain containing up to 18 carbon atoms.
R₃ is C₅–C₆ cycloalkylene or a straight-chained or branched, saturated or unsaturated aliphatic hydrocarbon chain containing 2–8 carbon atoms, which is unsubstituted or substituted one or more times by hydroxyl, phenyl, alkoxy-carbonyl, alkylthio, acylated amino or by alkoxy which is unsubstituted or is substituted by phenyl or alkoxy,
R₄ is —CH₂—CH₂,
R₅ is a hydrogen atom or a lower alkyl radical and
n is 0, 1 or 2; and
the pharmacologically acceptable salts thereof.

2. Compound as claimed in claim 1, wherein X is oxygen.

3. Compound as claimed in claim 1, wherein Y is oxygen.

4. Compound as claimed in claim 1, wherein Y is sulfur.

5. Compound as claimed in claim 1, wherein $R_5$ is hydrogen.

6. Compound as claimed in claim 1, wherein $R_5$ is lower alkyl.

7. Compound as claimed in claim 1, wherein n is 0.

8. Compound as claimed in claim 1, wherein n is 1.

9. Compound as claimed in claim 1, wherein n is 2.

10. Compound as claimed in claim 1, wherein $R_1$, $R_2$, $R_3$, X and Y have the given meanings and $R_4$ is a —CH$_2$—CH$_2$—chain, $R_5$ is a methyl radical and n is 0.

11. Compound as claimed in claim 1, wherein $R_5$ is a methyl radical, Y is an oxygen atom, and n is 0.

12. Compound as claimed in claim 1, wherein $R_1$, $R_2$, $R_4$, X, Y and n have the given meanings and $R_3$ is a —CH$_2$—CH$_2$—CH$_2$— chain or a —CH$_2$—CH$_2$—CH$_2$— chain wherein the middle carbon atom is substituted by hydroxyl, lower alkyl, lower alkoxy, or lower alkoxy or lower alkyl substituted by alkoxy.

13. Compound as claimed in claim 1 designated 2-methoxy-3-octadecylthiopropan-1-ol phosphoric acid monocholine ester.

14. Compound as claimed in claim 1 designated 3-(4-tridecyloxybutylthio)-propan-1-ol phoshoric acid monocholine ester.

15. Compound as claimed in claim 1 designated 3-hexadecylthio-2-methoxymethylpropan-1-ol phosphoric acid monocholine ester.

16. Compound as claimed in claim 1 designated 2-methyl-2-methoxycarbonyl-3-hexadecylthiopropan-1-ol phosphoric acid monocholine ester.

17. Compound as claimed in claim 1 designated 3-hexadecylthio-2-(2-methoxyethoxy)-propan-1-ol phosphoric acid monocholine ester.

18. Pharmaceutical composition having antitumor activity which composition comprises a pharmaceutically acceptable carrier and, in effective amount, an alkanol phosphoric acid monoammonium alkyl ester compound of the formula $$R_1-X-R_2-S(O)_n-R_3-Y-\overset{\overset{O}{\|}}{\underset{O^{\ominus}}{P}}-O-R_4-\overset{\oplus}{N}(R_5)_3$$

wherein

X is a valency bond, oxygen or sulfur, a sulfinyl or sulfonyl group, aminocarbonyl, carbonylamino or ureido group or a cycloalkylene or phenylene radical, Y is oxygen or sulfur, $R_1$ is hydrogen, straight-chained or branched, saturated or unsaturated aliphatic hydrocarbon chain containing up to 18 carbon atoms, which can be substituted one or more times by aryl, halogen, lower alkoxy, alkylthio, alkoxycarbonyl, alkanesulphinyl or alkanesulphonyl, $R_2$ is a straight-chained or branched, saturated or unsaturated aliphatic hydrocarbon chain containing up to 18 carbon atoms, which can be substituted one or more times by halogen, aryl, lower alkoxy, alkoxycarbonyl, alkylthio, alkanesulfinyl or alkanesulfonyl, $R_3$ is a straight-chained or branched, saturated or unsaturated aliphatic hydrocarbon chain containing 2–8 carbon atoms, which can also be part of a cycloalkane ring and can be substituted one or more times by hydroxyl, halogen, nitrile, cycloalkyl, phenyl, alkoxycarbonyl, optionally alkylated carbamoyl, alkylthio, alkanesulfinyl, alkanesulfonyl, optionally acylated amino or by alkoxy which, in turn, can be substituted by aryl, alkylthio, alkanesulfinyl, alkanesulfonyl, optionally acylated amino, alkoxy-carbonyl, nitrile, hydroxyl, alkoxy or optionally alkylated carbamoyl, $R_4$ is a straight-chained or branched alkylene containing 2 to 4 carbon atoms, $R_5$ is a hydrogen atom or a lower alkyl radical and n is 0, 1 or 2; and the pharmacologically acceptable salts thereof.

19. Composition as claimed in claim 18, wherein said compound is selected from the following 2-methoxy-3-octadecylthiopropan-1-ol phosphoric acid monocholine ester, 3-(4-tridecyloxybutylthio)-propan-1-ol phosphoric acid monocholine ester, 3-hexadecylthio-2-methoxymethylpropan-1-ol phosphoric acid monocholine ester, 2-methyl-2-methoxycarbonyl-3-hexadecylthiopropan-1-ol phosphoric acid monocholine ester, and 3-hexadecylthio-2-(2-methoxyethoxy)-propan-1-ol phosphoric acid monocholine ester.

20. Method of combating tumors which comprises administering to an afflicted subject an effective amount of an alkanol phosphoric acid monoammonium alkyl ester compound of the formula $$R_1-X-R_2-S(O)_n-R_3-Y-\overset{\overset{O}{\|}}{\underset{O^{\ominus}}{P}}-O-R_4-\overset{\oplus}{N}(R_5)_3$$

wherein

X is a valency bond, oxygen or sulfur, a sulfinyl or sulfonyl group, aminocarbonyl, carbonylamino or ureido group or a cycloalkylene or phenylene radical, Y is oxygen or sulfur, $R_1$ is hydrogen, straight chained or branched, saturated or unsaturated aliphatic hydrocarbon chain containing up to 18 carbon atoms, which can be substituted one or more times by aryl, halogen, lower alkoxy, alkylthio, alkoxycarbonyl, alkanesulphinyl or alkanesulphonyl, $R_2$ is a straight-chained or branched, saturated or unsaturated aliphatic hydrocarbon chain containing up to 18 carbon atoms, which can be substituted one or more times by halogen, aryl, lower alkoxy, alkoxycarbonyl, alkylthio, alkanesulfinyl or alkanesulfonyl, $R_3$ is a straight-chained or branched, saturated or unsaturated aliphatic hydrocarbon chain containing 2–8 carbon atoms, which can also be part of a cycloalkane ring and can be substituted one or more times by hydroxyl, halogen, nitrile, cycloalkyl, phenyl, alkoxycarbonyl, optionally alkylated carbamoyl, alkylthio, alkanesulfinyl, alkanesulfonyl, optionally acylated amino or by alkoxy which, in turn, can be substituted by aryl, alkylthio, alkanesulfinyl, alkanesulfonyl, optionally acylated amino, alkoxy-carbonyl, nitrile, hydroxyl, alkoxy or optionally alkylated carbamoyl, $R_4$ is a straight-chained or branched alkylene containing 2 to 4 carbon atoms, $R_5$ is a hydrogen atom or a lower alkyl radical and n is 0, 1 or 2; and the pharmacologically acceptable salts thereof.

21. Method as claimed in claim 20, wherein said compound is selected from 2-methoxy-3-octadecylthiopropan-1-ol phosphoric acid monocholine ester, 3-(4-tridecyloxybutylthio)-propan-1-ol phosphoric acid monocholine ester, 3-hexadecylthio-2-methoxymethylpropan-1-ol phosphoric acid monocholine ester, 2-methyl-2-methoxycarbonyl-3-hexadecylthio-propan-1-ol phosphoric acid monocholine ester, and 3-hexadecylthio-2-(2-methoxyethoxy)-propan-1-ol phosphoric acid monocholine ester.

* * * * *